(12) United States Patent
Apperson et al.

(10) Patent No.: US 12,171,453 B2
(45) Date of Patent: Dec. 24, 2024

(54) CONTROL SYSTEM FOR AN ULTRASONIC SURGICAL HANDPIECE

(71) Applicant: Kogent Surgical, LLC, Chesterfield, MO (US)

(72) Inventors: Steven J Apperson, Ballwin, MO (US); David G Wuchinich, Bronx, NY (US)

(73) Assignee: Kogent Surgical, LLC, Chesterfield, MO (US)

( * ) Notice: Subject to any disclaimer, the term of this patent is extended or adjusted under 35 U.S.C. 154(b) by 1421 days.

(21) Appl. No.: 16/593,603

(22) Filed: Oct. 4, 2019

(65) Prior Publication Data

US 2020/0253631 A1 Aug. 13, 2020

Related U.S. Application Data

(60) Provisional application No. 62/741,942, filed on Oct. 5, 2018.

(51) Int. Cl.
| | |
|---|---|
| *A61B 17/32* | (2006.01) |
| *A61B 17/00* | (2006.01) |
| *B06B 1/02* | (2006.01) |
| *H03K 5/26* | (2006.01) |

(52) U.S. Cl.
CPC .... *A61B 17/320068* (2013.01); *B06B 1/0207* (2013.01); *B06B 1/0223* (2013.01); *B06B 1/0253* (2013.01); *H03K 5/26* (2013.01); *A61B 2017/00199* (2013.01); *A61B 2017/00486* (2013.01); *A61B 2017/00973* (2013.01); *A61B 2017/32007* (2017.08); *A61B 2017/320084* (2013.01); *B06B 2201/76* (2013.01)

(58) Field of Classification Search
CPC . B06B 1/0253; B06B 1/0207; B06B 2201/76; B06B 2017/320084; B06B 2017/00973; B06B 2017/00486; B06B 2017/00199; B06B 2017/32007; B06B 2017/320068; H03K 5/26
See application file for complete search history.

(56) References Cited

U.S. PATENT DOCUMENTS 6,083,191 A * 7/2000 Rose ............... B06B 1/0261
606/169
2011/0266124 A1* 11/2011 Culp ............... A61B 17/1626
200/335

* cited by examiner

*Primary Examiner* — J. San Martin
(74) *Attorney, Agent, or Firm* — Jay J. Hoette; The Small Patent Law Group, LLC

(57) ABSTRACT

A control system for an ultrasonic surgical device has a console operatively connected to a power source and configured for detachable connection to the ultrasonic surgical device. A control circuit of the console is configured to regulate an operating signal to correspond to the operating characteristics of the ultrasonic surgical handpiece in response to a loading signal. An operator input of the console operatively connects to the control circuit to provide a control signal.

21 Claims, 17 Drawing Sheets

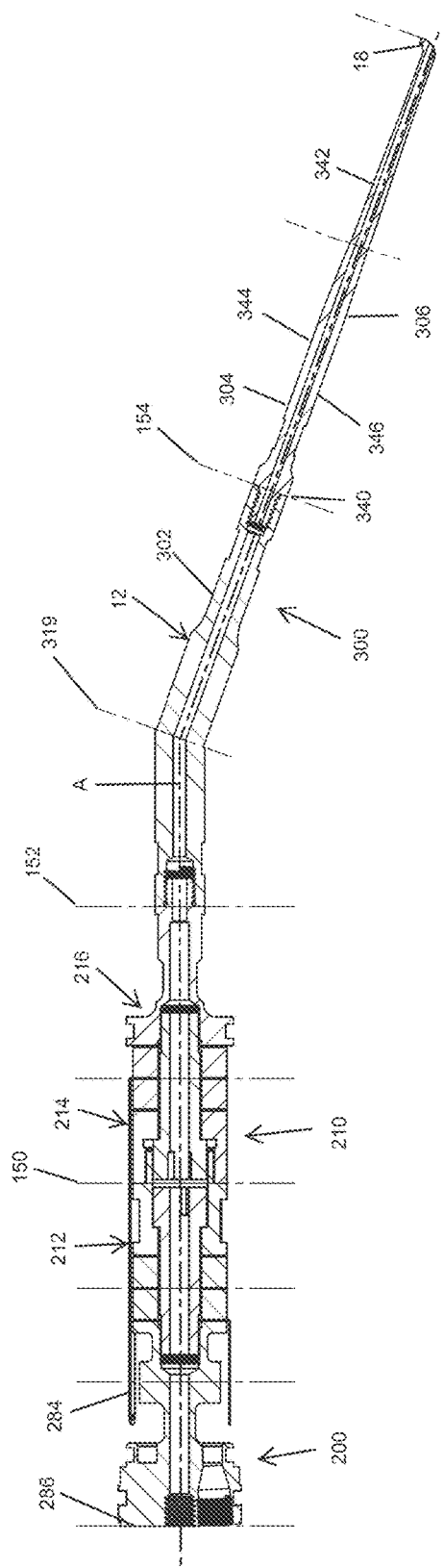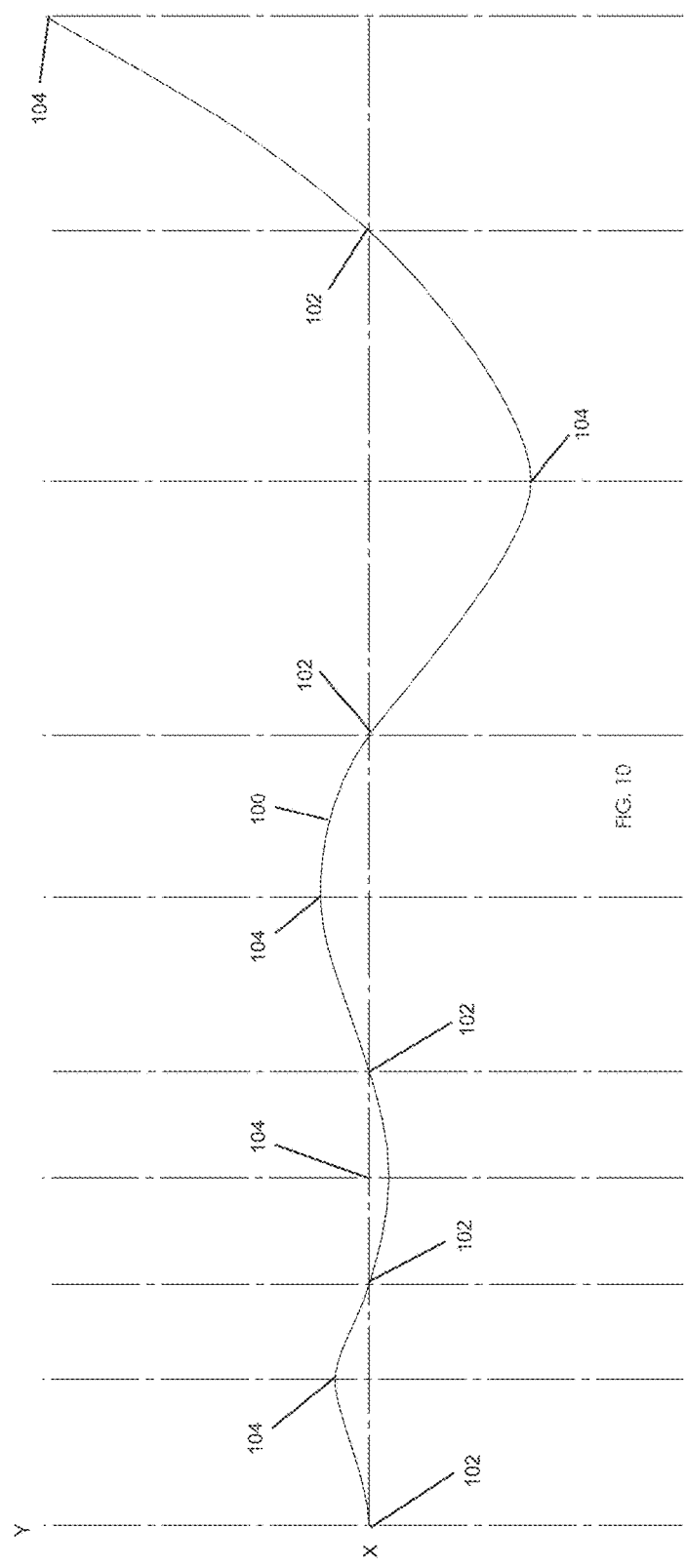
FIG. 10

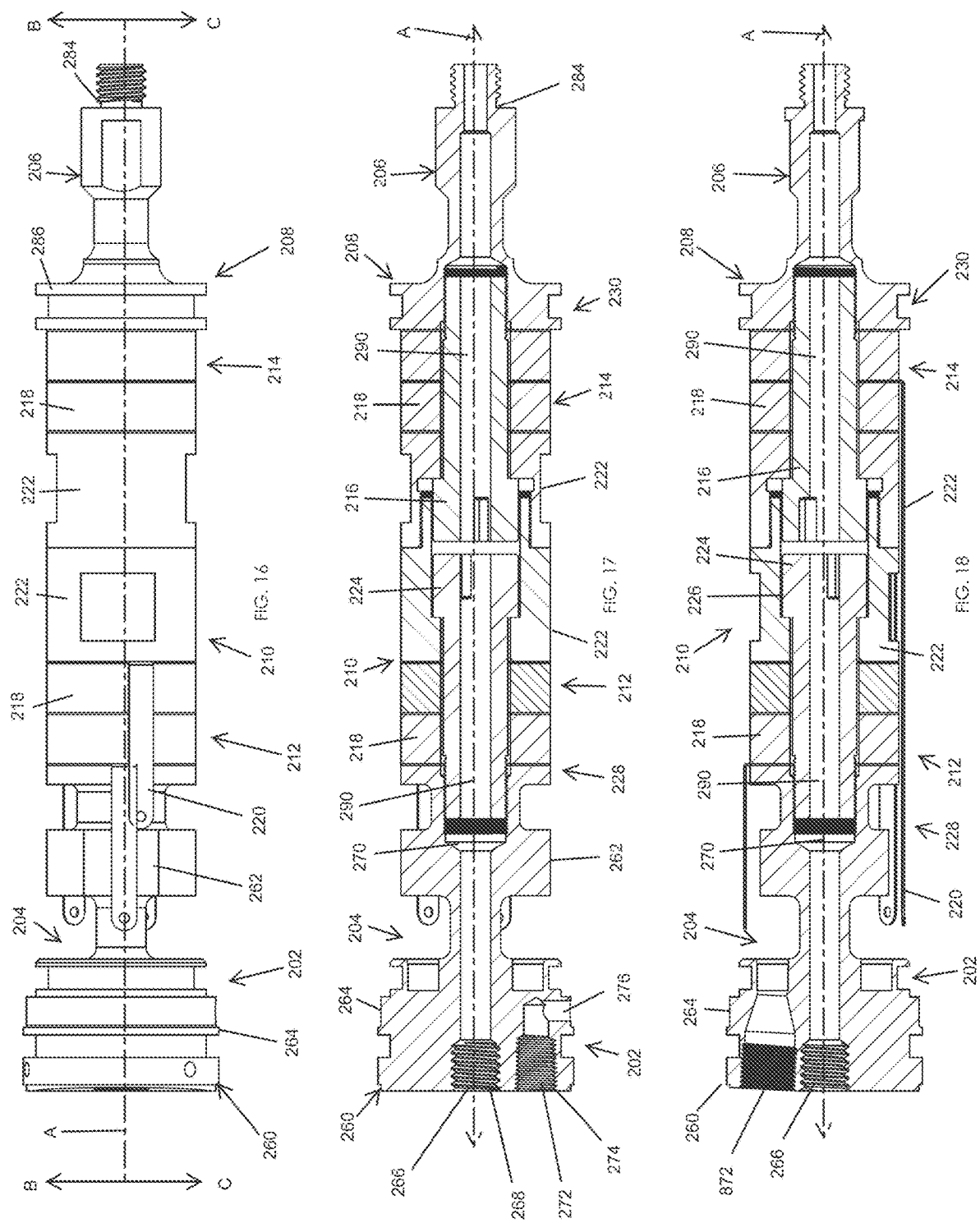

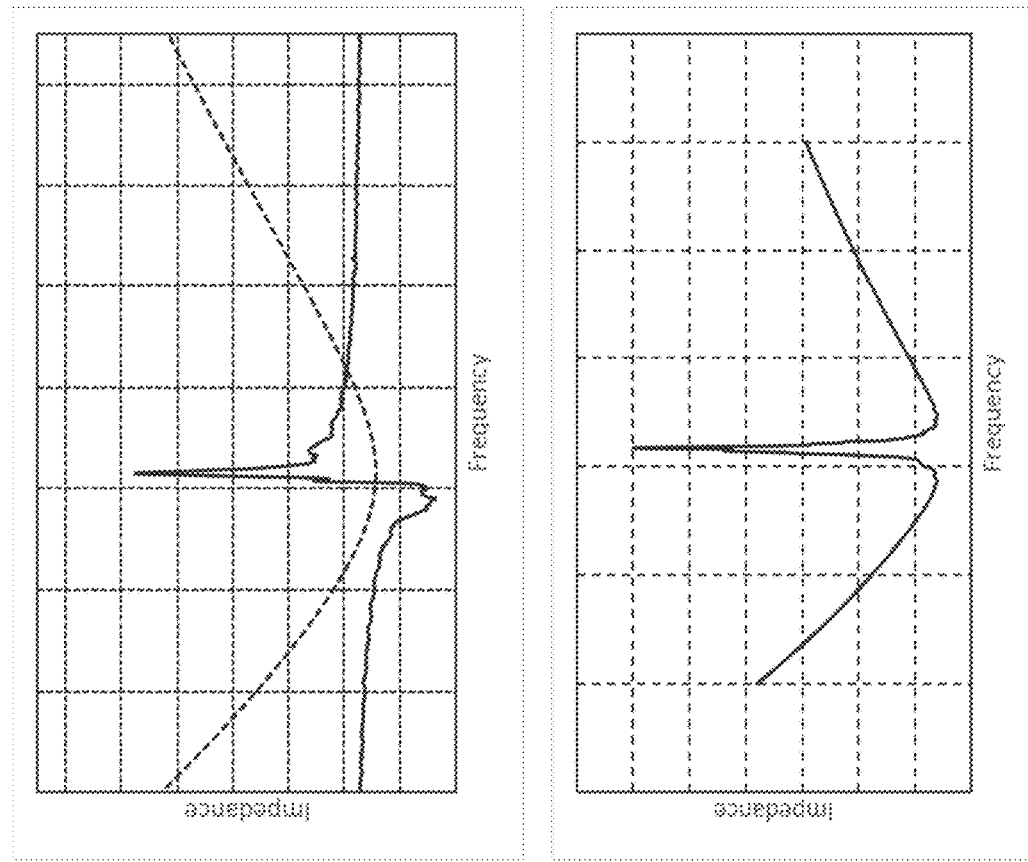
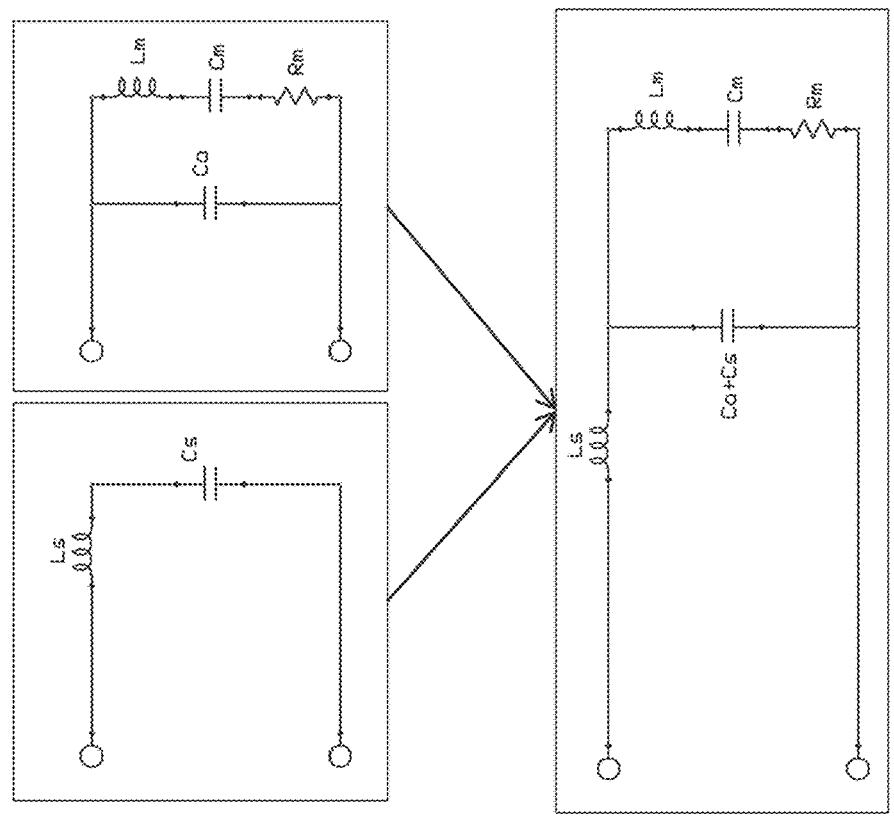
Fig. 24

CONTROL SYSTEM FOR AN ULTRASONIC SURGICAL HANDPIECE

CROSS-REFERENCE TO RELATED APPLICATIONS

Not applicable.

STATEMENT REGARDING FEDERALLY SPONSORED RESEARCH

Not applicable.

BACKGROUND

The present invention relates to a control system for an ultrasonic surgical device, and more particularly, the present invention relates to a control system that calibrates and maintains an operating signal that corresponds to the operating characteristics of the ultrasonic surgical handpiece Ultrasonic surgical systems are used in surgical procedures for various applications, such as, dissection, aspiration, coagulation, and cutting of biological tissue. Typically, ultrasonic surgical systems include an ultrasonic surgical device, sometimes referred to as an ultrasonic surgical handpiece, for use by the surgeon to engage biological tissue and a control system to provide power and an operating signal to the ultrasonic surgical handpiece.

Typically, an ultrasonic handpiece uses piezoelectric transducers to generate a high frequency wave oscillation that vibrates various surgical tools at a resonance frequency. Generally, resonance can be defined as the time harmonic exchange of the strain energy of the distributed elasticity with the motional energy of the movement of a structure's distributed elasticity and mass. The vibration may be longitudinal, radial, flexural, torsional or a combination of such forms of vibration. For purposes of physical analysis, such vibration can be mathematically represented as a standing wave which itself is composed of two waves of either strain or motion, with each of the two waves, either of strain or motion, superimposed upon the structure, each traveling in the opposite direction from the other, resulting in the formation of points of no motion and maximum strain (nodes) and of maximum motion and minimum or vanishing strain (anti-nodes).

Generally, a control system for an ultrasonic surgical handpiece provides an operating signal with a predetermined set of characteristics to match the characteristics of the ultrasonic surgical handpiece to be used. When the characteristics match, the ultrasonic surgical handpiece operates efficiently and optimally. For example, the control system may output an operating signal having a narrow frequency range that corresponds with the resonance frequency of the ultrasonic surgical handpiece. As a result, the vibration or amplitude of the ultrasonic surgical handpiece is large relative to the power being provided. However, when the characteristics do not match, the performance of the ultrasonic surgical handpiece diminishes in efficiency and functionality. For example, when control system outputs an operating signal with a frequency range that does not correspond with the resonance frequency of the ultrasonic surgical handpiece, the vibration or amplitude of the ultrasonic surgical handpiece is small relative to the power signal being provided. As a result, the ultrasonic surgical handpiece operates inefficiently or may not function properly. Consequently, to operate properly the control system and the ultrasonic surgical handpiece must be manually calibrated to have matching characteristics prior to use. Alternatively, the control system and ultrasonic handpiece may include additional components, such as memory components, RFID components, and the like to communicate the characteristics therebetween. In either case, the control system must be recalibrated each time a different ultrasonic surgical handpiece with different characteristics is selected, thereby adding to time, expense, and administration of the system.

During operation of the control system and the ultrasonic surgical handpiece, the operating characteristics of the ultrasonic surgical handpiece may fluctuate due to various factors. For example, the resonant frequency of the ultrasonic surgical handpiece may fluctuate as a function of thermal expansion from heat build-up during operation, power or signal fluctuations, and/or environmental factors, such as temperature and humidity. However, the control system does not adjust the operating signal to correspond to the changes in the operating characteristics of the ultrasonic surgical handpiece during operation. Therefore, even when correctly calibrated the ultrasonic surgical handpiece may not function efficiently or properly due to divergence between the characteristics of the operating signal and the operating characteristics of the ultrasonic surgical handpiece.

Therefore, there is a need for a control system for an ultrasonic surgical handpiece that automatically calibrates and maintains an operating signal that corresponds to the operating characteristics of the ultrasonic surgical handpiece.

BRIEF DESCRIPTION

In one embodiment, a control system for an ultrasonic surgical device includes a console operatively connected to a power source and is configured for detachable connection to the ultrasonic surgical device. A control circuit of the console is configured to regulate an operating signal to correspond to the operating characteristics of the ultrasonic surgical handpiece in response to a loading signal. An operator input of the console operatively connects to the control circuit to provide a control signal.

In another embodiment, a method for operating an ultrasonic surgical device, includes generating a generating signal at a drive frequency with a drive signal generator, generating a drive signal having a drive voltage and a drive current with a drive amplifier in response to the generating signal comparing the drive voltage and the drive current with a first phase comparator, generating a phase adjustment signal with the first phase comparator based on the comparison of the drive voltage and the drive current, generating a tuned drive signal with a drive tuning circuit in response to the phase adjustment signal, generating an operating signal with a handpiece loading circuit to operate the ultrasonic surgical device, generating a loading signal with the handpiece loading circuit, comparing the drive current to the loading signal with a second phase comparator, generating a frequency adjustment signal with the second phase comparator based on the comparison of the drive current and the loading signal; and regenerating the generating signal at an adjusted drive frequency with the drive signal generator in response to the frequency adjustment signal.

BRIEF DESCRIPTION OF THE DRAWINGS

The present inventive subject matter will be better understood from reading the following description of non-limiting embodiments, with reference to the attached drawings, wherein below:

FIG. 10 is a cross-section view of the ultrasonic surgical handpiece with housing removed taken along section A-A shown in FIG. 9 and a corresponding schematic illustrating a standing wave along the ultrasonic surgical handpiece in accordance with an embodiment;

FIG. 16 is a side view of a motor;

FIG. 17 is a cross-section view of the motor taken along section B-B shown in FIG. 16; and FIG. 18 is a cross-section view of the motor taken along section C-C shown in FIG. 16.

FIG. 24 illustrates the impendence and frequency of the control circuit.

Corresponding reference numerals indicate corresponding parts throughout the several figures of the drawings.

DETAILED DESCRIPTION

Figure 1:
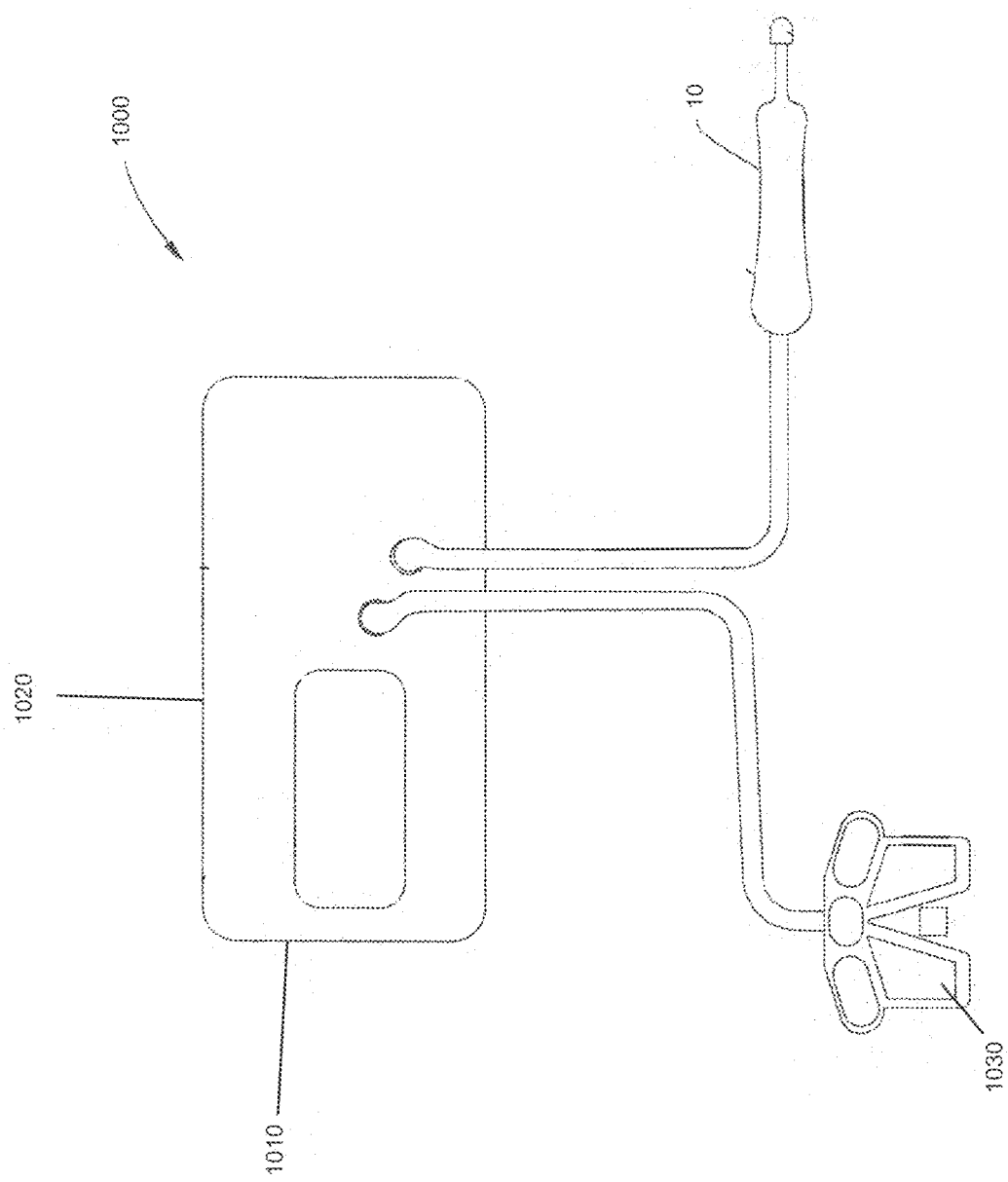
FIG. 1 is a schematic of an ultrasonic surgical system.

The following detailed description illustrates the inventive subject matter by way of example and not by way of limitation. The description enables one of ordinary skill in the art to make and use the inventive subject matter, describes several embodiments of the inventive subject matter, as well as adaptations, variations, alternatives, and uses of the inventive subject matter. Additionally, it is to be understood that the inventive subject matter is not limited in its application to the details of construction and the arrangements of components set forth in the following description or illustrated in the drawings. The inventive subject matter is capable of other embodiments and of being practiced or being carried out in various ways. Also, it is to be understood that the phraseology and terminology used herein is for the purpose of description and should not be regarded as limiting on all embodiments of the inventive subject matter.

The terminology used herein is for the purpose of describing particular exemplary embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The steps, processes, and operations described herein are not to be construed as necessarily requiring their respective performance in the particular order discussed or illustrated, unless specifically identified as a preferred order of performance. It is also to be understood that additional or alternative steps may be employed.

Embodiments described herein include ultrasonic surgical systems that have control systems, surgical handpieces, motors, and surgical attachments used in surgical procedures to engage biological tissue. For example, the ultrasonic surgical system may have a control system having a console operatively connected to a power source and configured for detachable connection to the ultrasonic surgical device. The console may have a control circuit configured to regulate an operating signal to correspond to the operating characteristics of the ultrasonic surgical handpiece in response to a loading signal; The console may also include an operator input operatively connected to the control circuit to provide a control signal. In addition, the ultrasonic surgical system may have a surgical handpiece with a motor having a torsional transducer assembly. The torsional transducer assembly may have a variety of configurations as set forth herein. For example, the transducer assembly may be configured to create a standing wave along the central axis of the surgical handpiece in response to the application of an electrical current and voltage from a power source or control system. The standing wave may define an alternating pattern of nodes and anti-nodes along the central axis with a position of one of the anti-nodes corresponds with the position of a working plane of a surgical attachment that engages biological tissue, including both soft and hard tissue. The surgical attachment may have a variety of configurations as set forth herein. Optionally, the ultrasonic surgical system may include an irrigation assembly and/or an aspiration assembly to irrigate and/or aspirate the biological tissue.

FIG. 1 is a schematic of an ultrasonic control system 1000. The control system 1000 includes an ultrasonic console 1010 connected to a power source (not shown), and detachably connected to an ultrasonic surgical device 10. The console 1010 includes a control circuit 1020 configured to regulate an operating signal that corresponds to the operating characteristics of the ultrasonic surgical handpiece 10 in response to a loading signal from the handpiece 10. The control system 1000 may also include an operator input 1030, such as a footpedal, operatively connected to the control circuit to provide a control signal based on input from a user.

Figure 2:
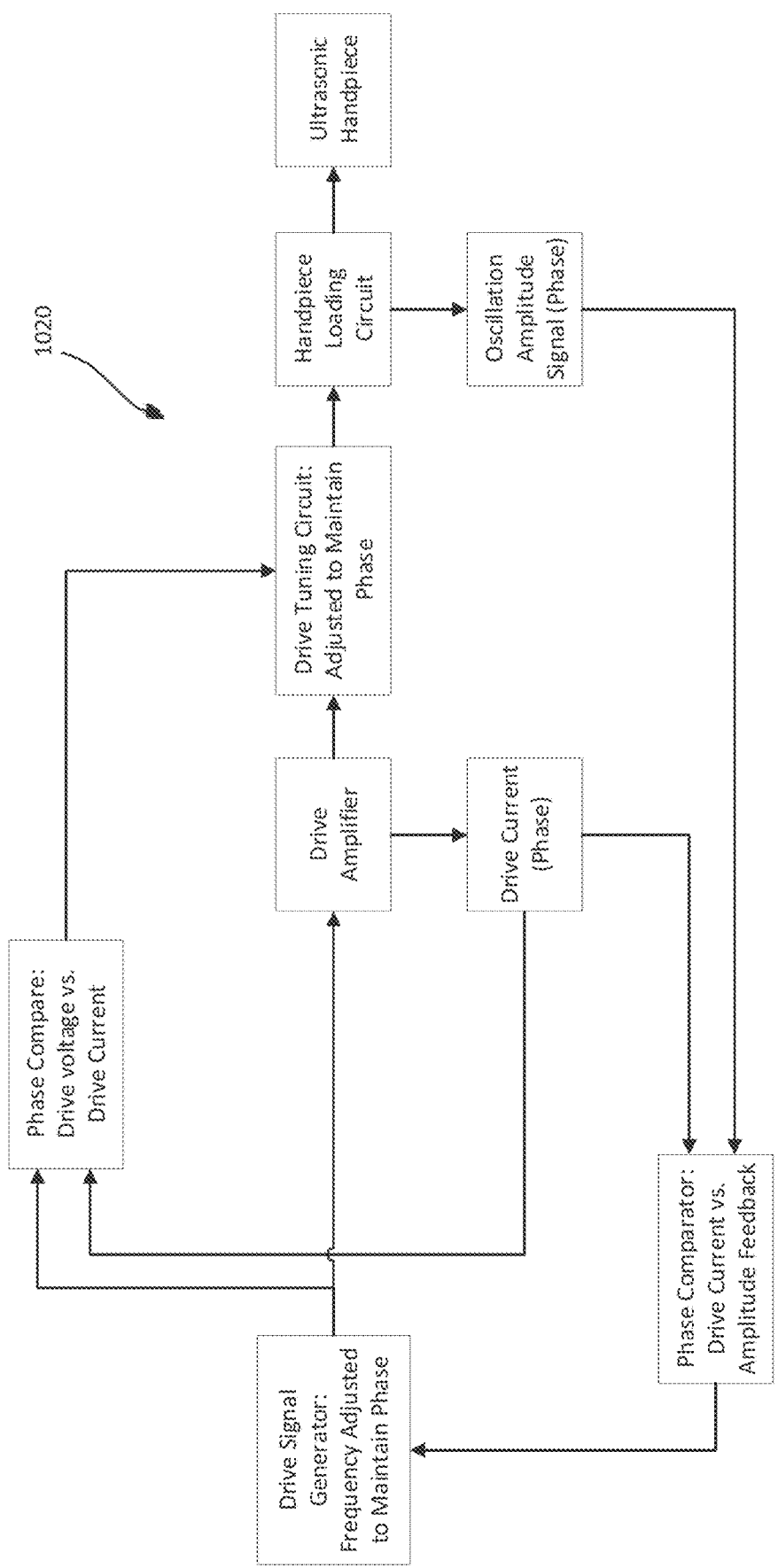
FIG. 2 is a block diagram of a control circuit.

FIG. 2 is a block diagram of the control circuit 1020 of the ultrasonic control system 1000. In an exemplary embodiment, the control circuit 1020 is a combination of an analog circuit configured to increase power in response to a load with a digital circuit configured to automatically adjust a center frequency of the analog circuit to a resonance frequency of the surgical handpiece. A current limited maintaining drive of the surgical handpiece, FPGA implantation of digital controls. The control circuit 1020 is configured to automatically maintain the frequency signal in a predetermined range of the resonance frequency of the surgical handpiece 10. Accordingly, the control circuit 1020 is configured to provide increased power during operation.

The control circuit 1020 includes a drive signal generator configured to produce a generating signal at a drive frequency; a drive amplifier operatively connected to the drive signal generator, the drive amplifier configured to provide a drive signal having a drive voltage and a drive current in response to the operating signal; a first phase comparator operatively connected to the drive signal generator and operatively connected to the drive amplifier, the first phase comparator configured to provide a phase adjustment signal based on a comparison of the drive voltage and the drive current; a drive tuning circuit operatively connected to the drive amplifier and configured to provide a tuned drive signal in response to the phase adjustment signal; a handpiece loading circuit operatively connected to the drive tuning circuit and operatively connected to the ultrasonic surgical handpiece, the handpiece loading circuit being configured to provide an operating signal to the ultrasonic surgical device, and provide a loading signal in response to the operating characteristics of the ultrasonic surgical device; and a second phase comparator operatively connected to the drive amplifier and operatively connected to the handpiece loading circuit, the second phase comparator being configured provide a frequency adjustment signal to the drive signal generator based on a comparison of the drive current to the loading signal.

Figure 3:
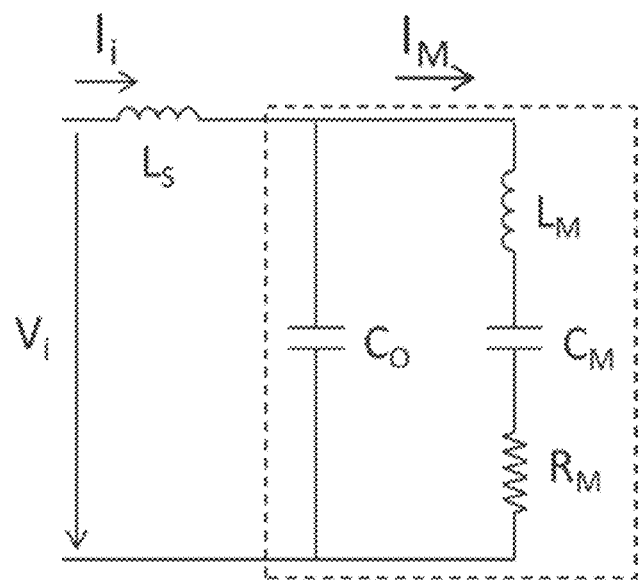
FIG. 3 is a schematic of an equivalent circuit for a piezoelectric transducer driven through inductance.
Figure 4:
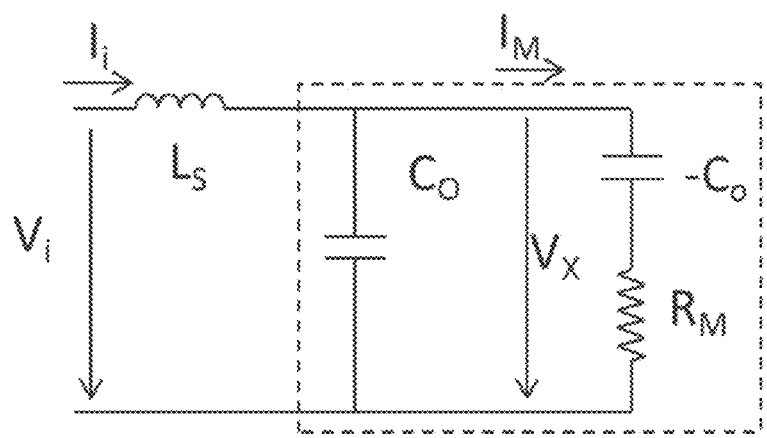
FIG. 4 is a schematic of an equivalent circuit for a piezoelectric transducer in parallel resonance.

FIG. 3 is a schematic of an equivalent circuit for a piezoelectric transducer driven through inductance. As shown, $C_O$ is the electrical capacitance of the crystals used and the m subscript refers to quantities whose physical origin is mechanical but are reflected as electrical components. $C_M$ is the equivalent capacitance of the entire transducer and $L_M$ is the energy equivalent mass. $I_M$, the electrical current flowing through the reflected quantities, is proportional to the transducer tip velocity (amplitude). Kinsler and Frey (2nd Ed.) provides a development of this representation, which is hereby incorporated by reference FIG. 4 is a schematic of an equivalent circuit for a piezoelectric transducer in parallel resonance. In the condition known as anti-resonance, or parallel resonance, $$\frac{1}{j\omega_z C_M} + j\omega_s L_M = -\frac{1}{j\omega_z C_o},$$

and the circuit appears as shown in FIG. 4. This can be reduced as shown in FIG. 5, which is a schematic of an alternate equivalent circuit for a piezoelectric transducer in parallel resonance.

Figure 5:
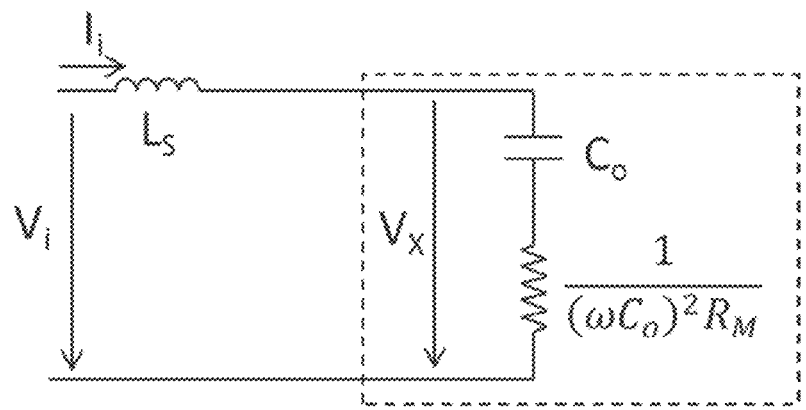
FIG. 5 is a schematic of an alternate equivalent circuit for a piezoelectric transducer in parallel resonance.
Figure 6:
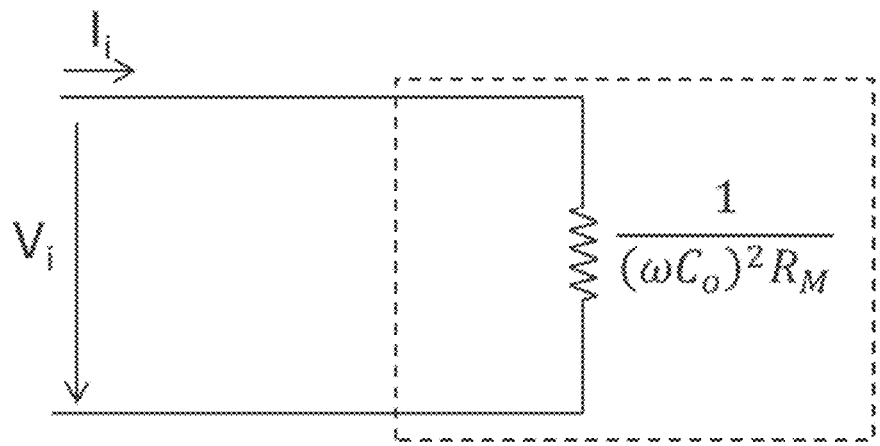
FIG. 6 is a schematic of an equivalent circuit for a piezoelectric transducer for series tuning.

FIG. 6 is a schematic of an equivalent circuit for a piezoelectric transducer with series tuned drive. For proper series tuning, $$L_s = \frac{1}{\omega_z C_o},$$

and the circuit of FIG. 5 be reduced as shown in

FIG. 6, which is a schematic of an equivalent circuit for a piezoelectric transducer with tuned drive. From this simplification, $$I_i = \frac{V_i}{\frac{1}{(\omega_z C_o)^2 R_M}} = V_i((\omega_z C_o)^2 R_M),$$

and the power delivered to the handpiece is $P=V_i*I_i=(\omega_s V_i C_p)^2(R_M)$. Since the input voltage, static capacitance, and anti-resonance of the handpiece are nominally constant, the power delivered will increase with increases in mechanical loading ($R_m$) of the tip. It can separately be shown that at anti-resonance, $I_M=-j\omega_s C_o V_i$. Which means that the transducer velocity ($I_M$) is independent of the mechanical load ($R_M$). This is the mathematical basis for how the generator increases the output power of the generator automatically to maintain constant amplitude of the tip. However, optimal series tuning is difficult to obtain given electrical tolerances of available inductors and capacitors for the tuning circuit, and the mechanical tolerances of the anti-resonant frequency of the transducers and tips.

Figure 7:
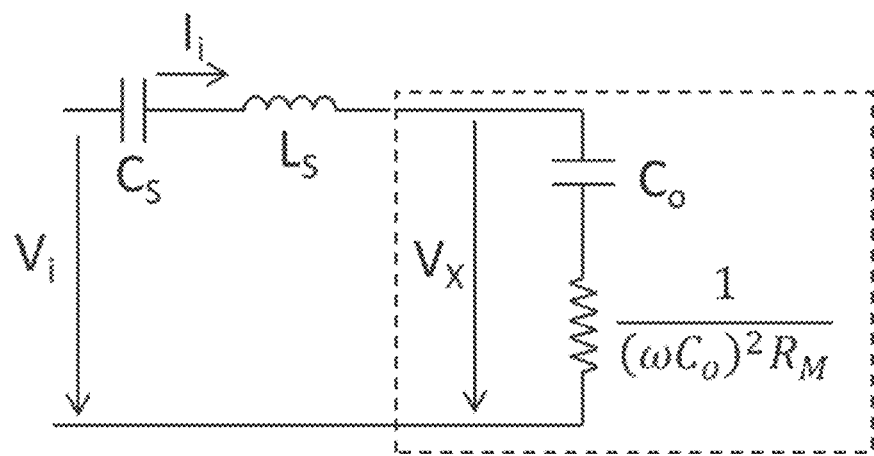
FIG. 7 is a schematic of an equivalent circuit for a piezoelectric transducer for series tuning.

Therefore, a series capacitance ($C_S$) is introduced as shown in FIG. 7, which is a schematic of an alternate equivalent circuit for a piezoelectric transducer with series capacitance; This can be reduced to the circuit shown in FIG. 8, where:

$$C_{eqv} = \frac{C_S C_o}{C_S + C_o}$$

And the series tuning frequency, $\omega_p$, is:

$$\omega_p = \frac{1}{\sqrt{L_S C_{eqv}}}$$

Making $C_s$ a multitude of electrically switchable capacitors allows electronic control of the series tuning frequency, and it can be automatically adjusted in a control loop to maintain the ideal phase difference between $V_i$, and $I_i$, which is that of the purely resistive load at antiresonance represented in FIG. 6.

FIG. 24 illustrates the impendence and frequency of the control circuit.

Figure 25:
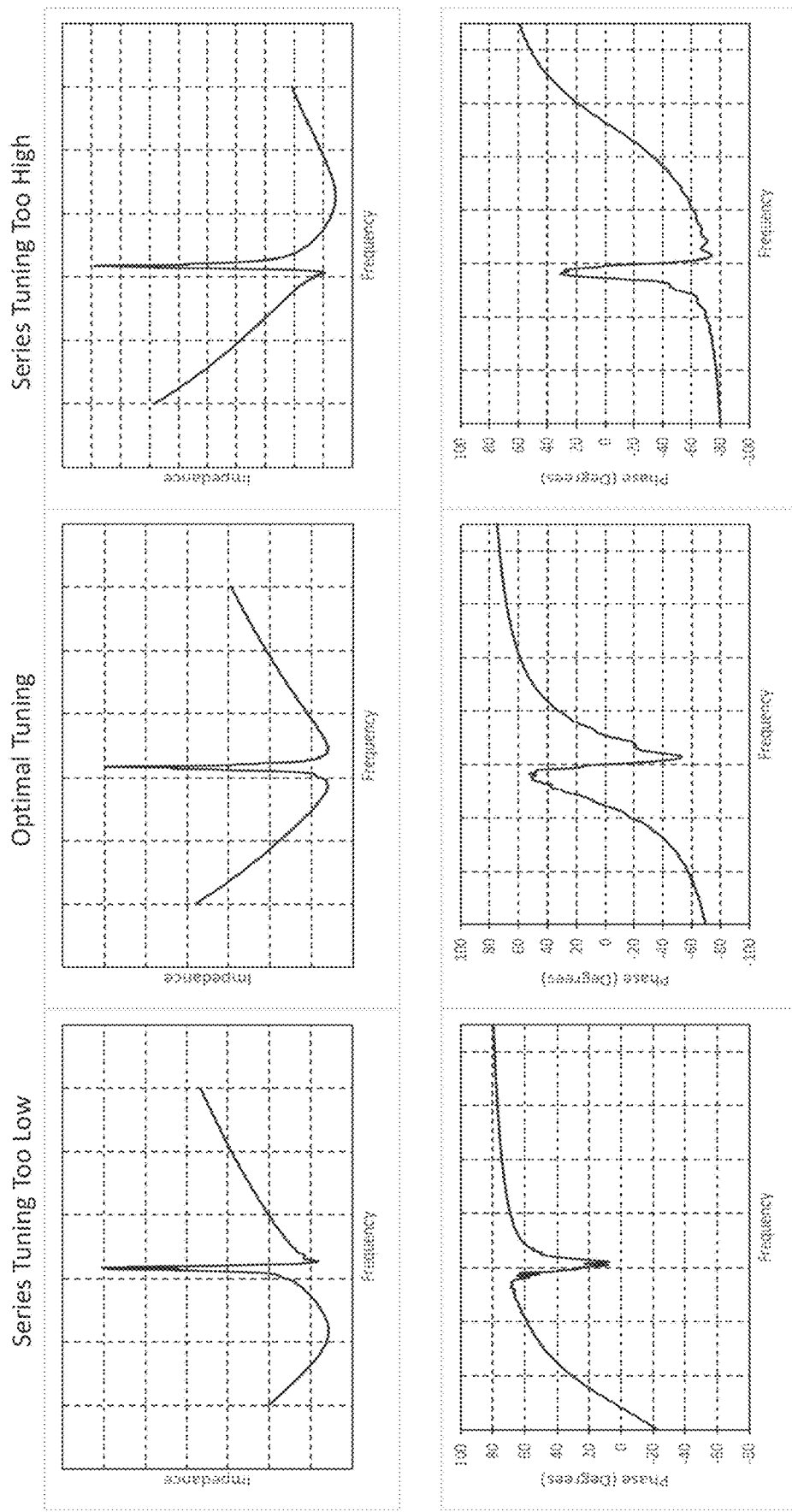
FIG. 25 illustrates the impendence and frequency of the control circuit in various states.

FIG. 25 illustrates the impendence and frequency of the control circuit in various states.

Figure 9:
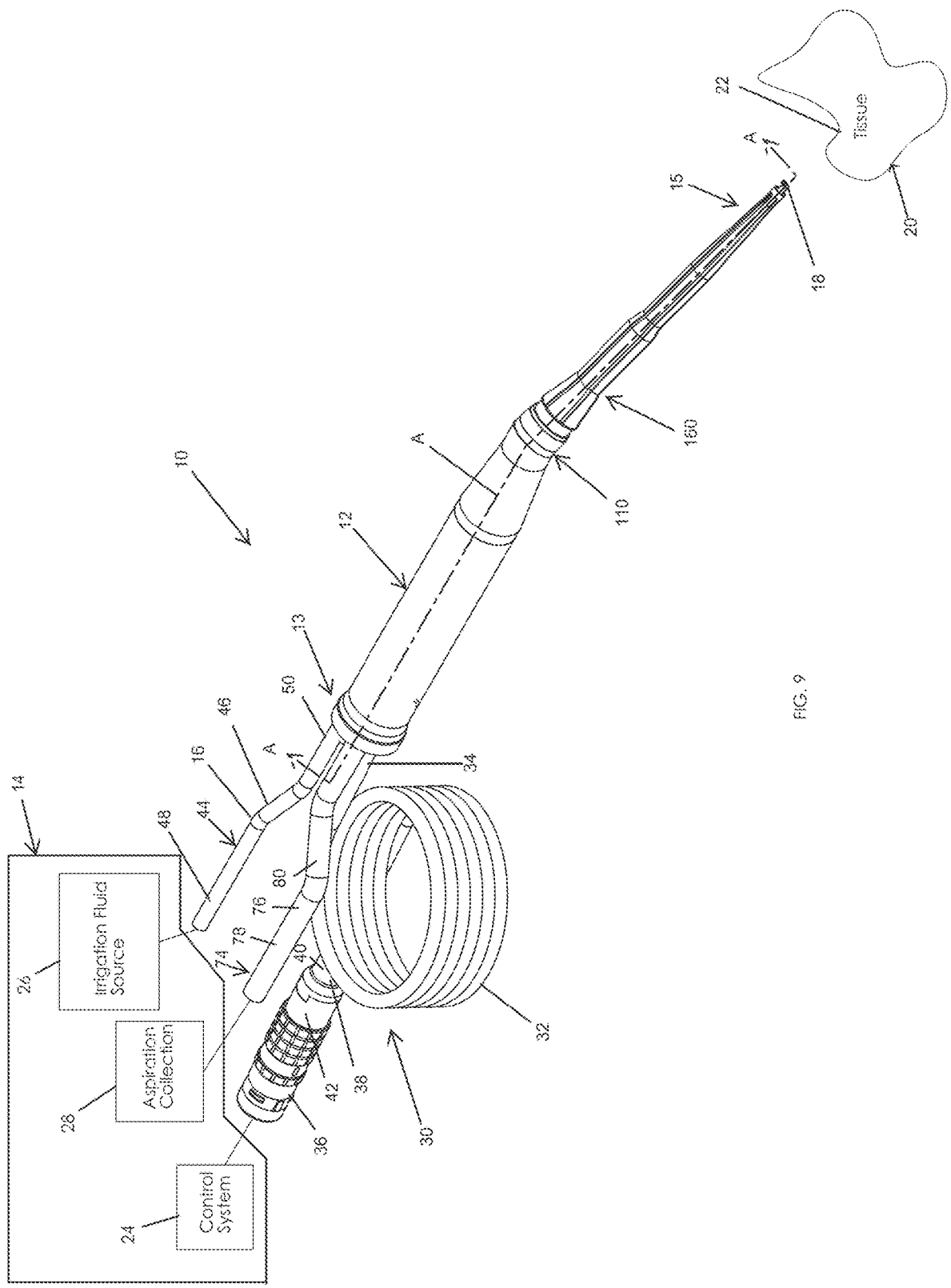
FIG. 9 is a perspective view of an ultrasonic surgical handpiece constructed in accordance with an embodiment.

FIG. 9 is a perspective view of an ultrasonic surgical system 10 constructed in accordance with an embodiment that includes a surgical handpiece 12 having a distal end 13 operatively connected to a control system 14 with a connection assembly 16. In an exemplary embodiment, the control system 14 is configured to provide power, irrigation fluid, and suction or aspiration at a working plane 18 of a proximal end 15 of the handpiece 12 during a surgical procedure. The working plane 18 of the handpiece 12 may engage biological tissue 20 at a surgical site 22 to perform various surgical procedures, such as, cutting coagulation, irrigation, and aspiration. In alternate embodiments, the handpiece 12 may be configured to engage soft biological tissue, such as, muscular tissue, connective tissue, nervous tissue, epithelial tissue, and the like, or hard biological tissue, such as, bone, enamel, dentin, cementum, and the like.

FIG. 10 is a cross-section view of the ultrasonic surgical handpiece 12 with housing removed taken along section A-A shown in FIG. 9 and a corresponding schematic illustrating the standing wave 100 along the ultrasonic surgical handpiece 12 in accordance with an embodiment. In response to the application of electrical current and voltage from the control system 14, the handpiece 12 creates a standing wave 100 along the central axis A with an alternating pattern of nodes 102 and anti-nodes 104 located at various positions along the central axis A. The X-axis of the schematic illustrates the position of the nodes 102 and anti-nodes along the central axis A of the handpiece 12. The Y-axis illustrates the amplitude of the standing wave 100 along the central axis A of the handpiece 12.

For example, anti-nodes 104 are located a proximal end 284 of a connector block 202, at an interface 150 between a first stack 212 and a second stack 214 of a transducer assembly 210, an interface 152 between an amplifier 206 and a surgical attachment 300, an interface 154 between an angled adapter 302 and an ultrasonic tip 304, and at the working plane 18. For example, the distance between anti-nodes 14 along the handpiece 12 are (from distal end to the proximal end) about 0.903" inches, about 0.5922" inches, about 0.658" inches, about 1.087" inches, about 1.057" inches, about 1.66" inches, about 1.626" inches, and about 1.365" inches. For example, the amplitude of the standing wave 100 progressively increases along the central axis A of the handpiece 12 approaching the proximal end 15 of the handpiece 12, with the maximum amplitude being at the working plane 18.

Generally, the standing wave 100 may be described as a wave that oscillates in time but whose peak amplitude profile does not move in space. The standing wave 100 may represent the distribution of motion along the length of the surgical handpiece 12 whose amplitude varies harmonically in time but remains spatially stationary. The peak amplitude of the wave oscillations at any point in space is constant in time, and the oscillations at different points throughout the wave are in phase with each other. The standing wave pattern defines an alternating pattern of nodal positions, such as nodes and anti-nodes. When a standing wave is established, the nodes and anti-nodes remain located at the same position along the medium. A node of the standing wave is a location at which the amplitude of the standing wave is minimum, which may include zero. At the nodes, there is minimal to no displacement during each vibrational cycle. The standing wave 100 may be formed by the interference of two traveling waves. Therefore, nodes are produced at locations where destructive interference occurs. An anti-node of the standing wave is a location at which the amplitude of the standing wave is maximum. At the anti-nodes, there is a maximum displacement during each vibrational cycle. The anti-node vibrates back and forth between a positive displacement and a negative displacement. Anti-nodes are produced at locations where constructive interference occurs.

Figure 11:
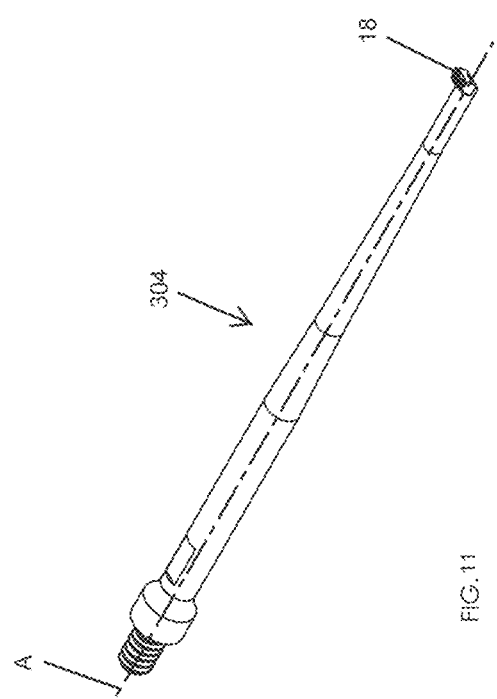
FIG. 11 is a perspective view of an ultrasonic tip in accordance with an embodiment.

FIG. 11 is a perspective view of an ultrasonic tip 304 in accordance with an embodiment.

Figure 12:
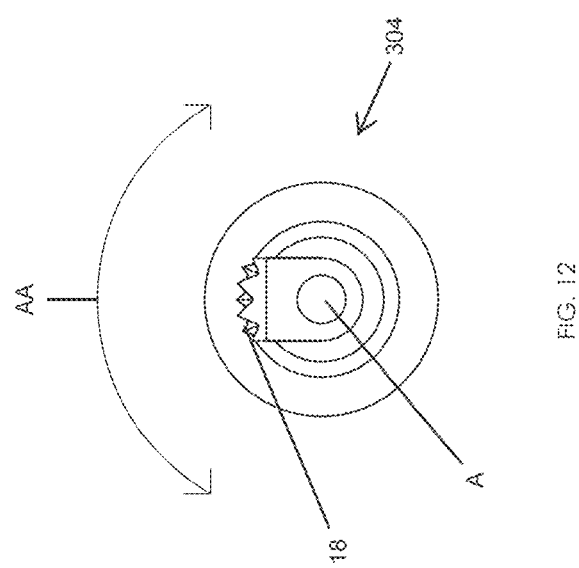
FIG. 12 is an end view of the ultrasonic tip illustrating torsional motion at a working plane in accordance with an embodiment.

FIG. 12 is an end view of the ultrasonic tip 304 illustrating torsional motion at the working plane 18 in accordance with an embodiment. The standing wave 100 created along the handpiece 12 results in torsional motion about the central axis A at the working plane 18 of the surgical attachment 300. For example, the amplitude AA of the tip 304 at the working plane 18 may be a maximum of about 18 mils peak-to-peak (450 microns) with an operating resonance frequency of about 24500 to 25500 Hz. However, alternate embodiments may produce other amplitudes at the working plane 18 and/or with other operating resonance frequencies.

Referring again to FIG. 9, the control system 14 includes a power source 24 that provides electrical current and power to the handpiece 12 via the connection assembly 16. For example, the handpiece 12 may have an operating frequency in a range of 24500 to 25500 Hz and be driven by the control system 14 with power in a range of 85 to 110 watts. In alternate embodiments, the handpiece 12 may have an operating frequency of less than 24500 Hz or greater than 25500 Hz and be driven with power of less than 85 watts or greater than 110 watts.

An exemplary embodiment of the control system 14 also includes an irrigation fluid source 26 configured to provide irrigation fluid to the handpiece 12 via the connection assembly 16. In one embodiment, the handpiece 12 may be configured to communicate irrigation fluid through one or more irrigation channels of the handpiece 12 to the working plane 18 and the surgical site 22 for use as a cooling medium and irrigation. For example, the irrigation fluid source 26 may include an irrigation pump (not shown), such as a peristaltic pump, configured to pump water from a water source to the handpiece 12 via the connection assembly 16.

In addition, an exemplary embodiment of the control system 14 includes an aspiration collector 28 to provide suction to the handpiece 12 via the connection assembly 16. In one embodiment, the handpiece 12 may be configured to provide suction through a suction channel of the handpiece 12 to the working plane 18 and the surgical site 22 for use as aspiration. For example, the aspiration collector 28 may include a vacuum pump (not shown), configured to create a vacuum to the handpiece via the connection assembly 16 to communicate aspirated biological tissue from the working plane 18 and surgical site 22 to a biological waste cannister (not shown).

In the illustrated embodiment, the connection assembly 16 includes an electrical connection 30 that transmits electrical power from the power source 24 of the control system 14 to the handpiece 12. For example, the electrical connection 30 includes an electrical cable 32 having a proximal end 34 coupled with the handpiece 12, and an electrical connector 36 attached to a distal end 38 of the cable 32. Optionally, a strain relief 40 is attached at a cable end 42 of the electrical connector 36. As illustrated, the electrical connector 36 is a high-voltage modular connector, such as, a connector manufactured by LEMO®, that detachably connects with the control system 14. However, in alternate embodiments, the connector may be any suitable connector capable of operatively connecting with the control system 14.

The connection assembly 16 also includes an irrigation connection 44 that transmits irrigation fluid from the irrigation fluid source 26 of the control system 14 to the handpiece 12. For example, the irrigation connection includes a tube 46 having a distal end 48 connected to the control system 14 and a proximal end 50 coupled with the handpiece 12, such as with an irrigation barb 52 (FIG. 13).

The connection assembly 16 also includes an aspiration connection 74 that transmits aspirated material from the handpiece 12 to the aspirator collector 28 of the control system 14. For example, the aspirator connection 74 includes a tube 76 having a distal end 78 connected to the control system 14 and a proximal end 80 coupled with the handpiece 12, such as with an aspiration barb 82 (FIG. 13).

In one or more embodiments, the irrigation barb 52 and/or the aspiration barb 82 may be manufactured from any suitable material, including, but not limited to, polymers, metals, metal alloys, any combination thereof. For example, irrigation barb 52 and/or the aspiration barb 82 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, irrigation barb 52 and/or the aspiration barb 82 may be manufactured from an underdamped material, a material having a Q factor greater than 0.5, a metal alloy in an annealed condition, a titanium alloy in an annealed condition, or from Ti-6Al-4V extra-low interstitials in an annealed condition.

Figure 13:
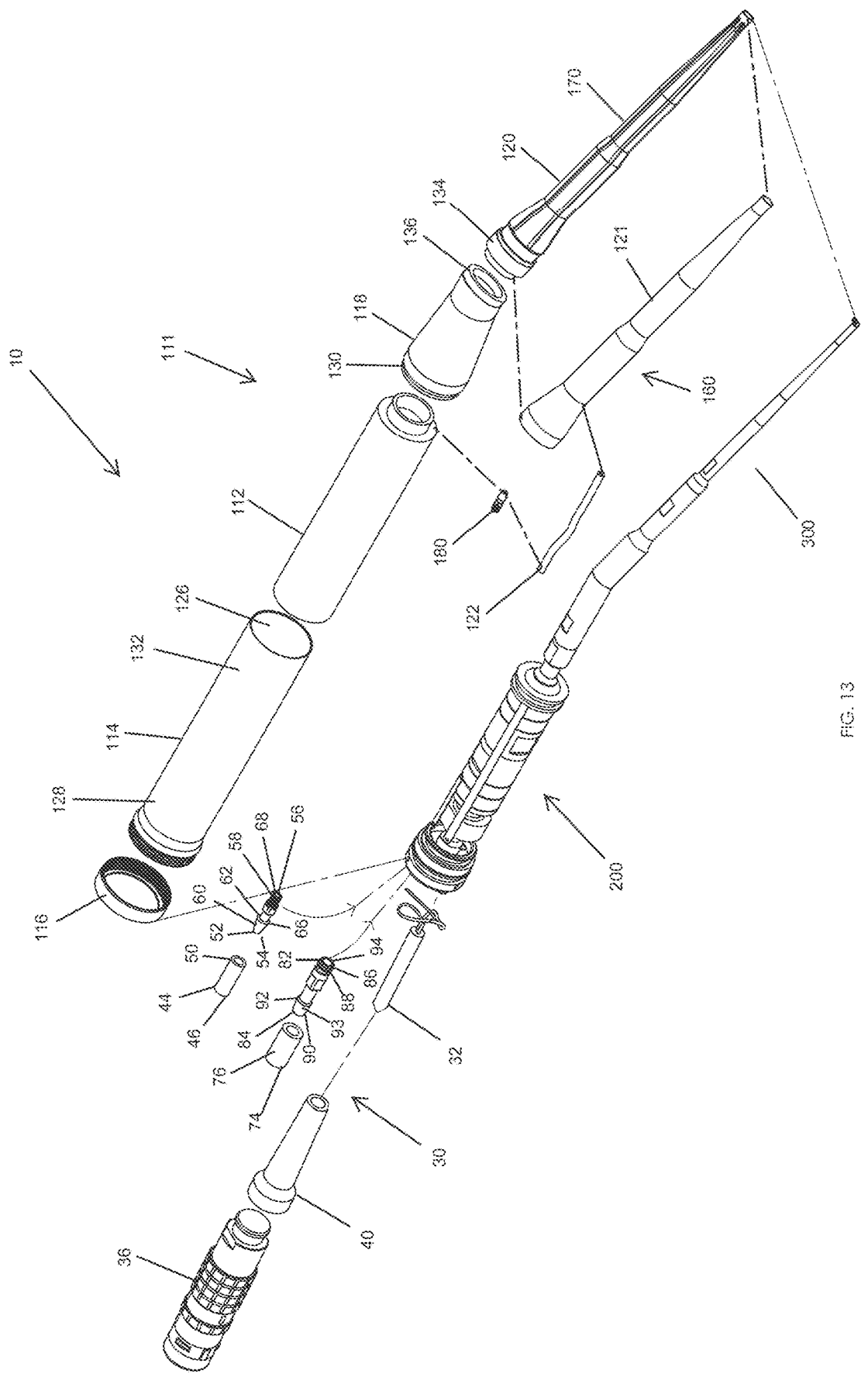
FIG. 13 is a partially exploded perspective view of an ultrasonic surgical handpiece with a housing removed and a connection assembly in accordance with an embodiment.
Figure 14:
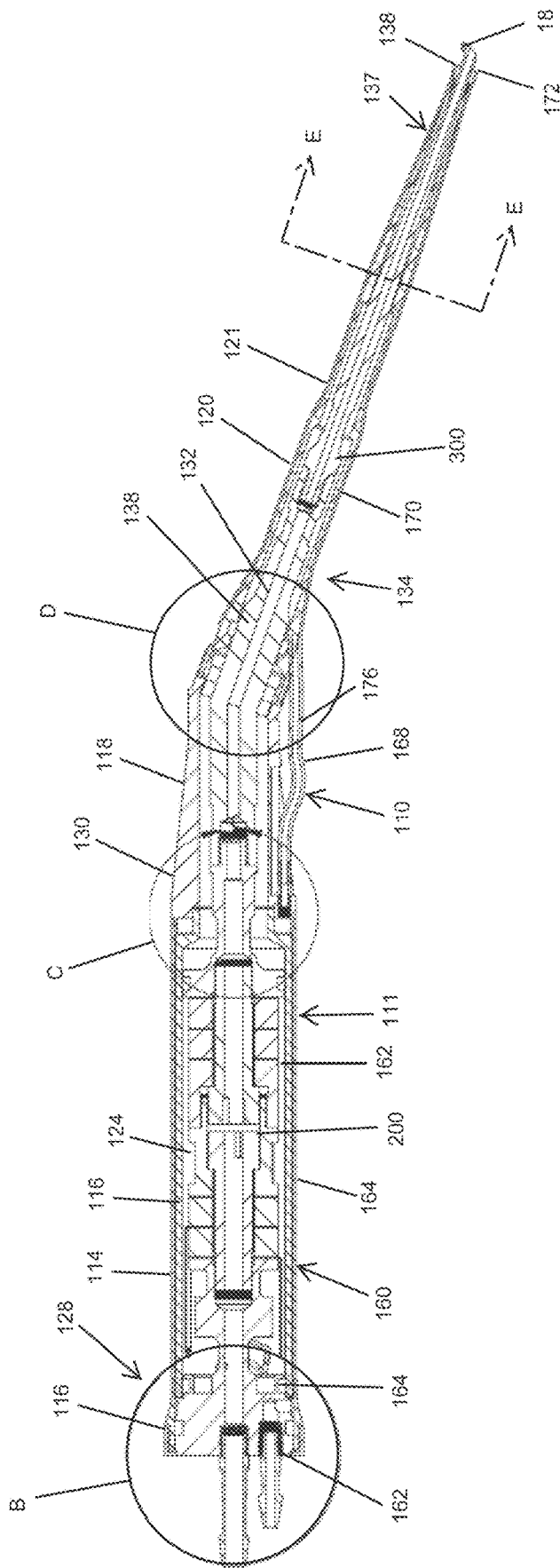
FIG. 14 is a cross-section view of the ultrasonic surgical handpiece taken along section A-A shown in FIG. 9.

FIG. 13 is a partially exploded perspective view of the ultrasonic surgical handpiece 12 with a housing 110 removed and a connection assembly in accordance with an embodiment that includes a motor 200 and a surgical attachment 300. FIG. 14 is a cross-section view of the ultrasonic surgical handpiece 12 taken along section A-A shown in FIG. 9. In an exemplary embodiment, the housing 110 includes an inner sleeve 112, and outer sleeve 114, a collar 116, a nose cone 118, and an irrigation sleeve 120, that detachably assemble to receive the motor 200 and the surgical attachment 300 and define an irrigation channel 122 (FIG. 14) that communicates irrigation fluid from the irrigation connection 44 to the working plane 18. For example, the generally cylindrical inner sleeve 112 includes a bore 124 configured to receive the motor 200. The generally cylindrical outer sleeve 114 includes a bore 126 configured to receive the inner sleeve 124 and motor 200 and defines a portion of the generally annular irrigation channel 122 between the inner sleeve 120 and the outer sleeve 122. The collar 116 detachably couples with a distal end 128 of the outer sleeve 114, such as with a threaded connection. The nosecone 118 includes a distal end 130 configured to detachably couple, such as with a threaded connection, with a proximal end 132 of the outer sleeve 126 and define a portion of the irrigation channel 122. The irrigation sleeve 120 includes a distal end 134 configured to detachably couple, such as with a threaded connection, with a proximal end 136 of the nosecone 118 and define a portion of the irrigation channel 122. A distal end 137 of the irrigation sleeve 120 defines an outlet 138 configured to direct irrigation fluid from the irrigation channel 122 to the working plane 18 and surgical site 22. In one or more embodiments, each component of the housing 110 may be manufactured from any suitable material, including, but not limited to, polymers, metals, metal alloys, any combination thereof.

Figure 8:
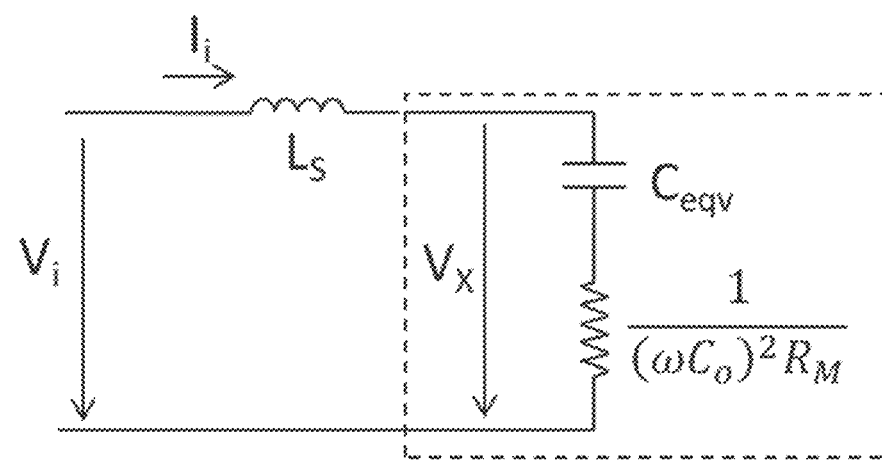
FIG. 8 is a schematic of an alternate equivalent circuit for a piezoelectric transducer with series capacitance.
Figure 15:
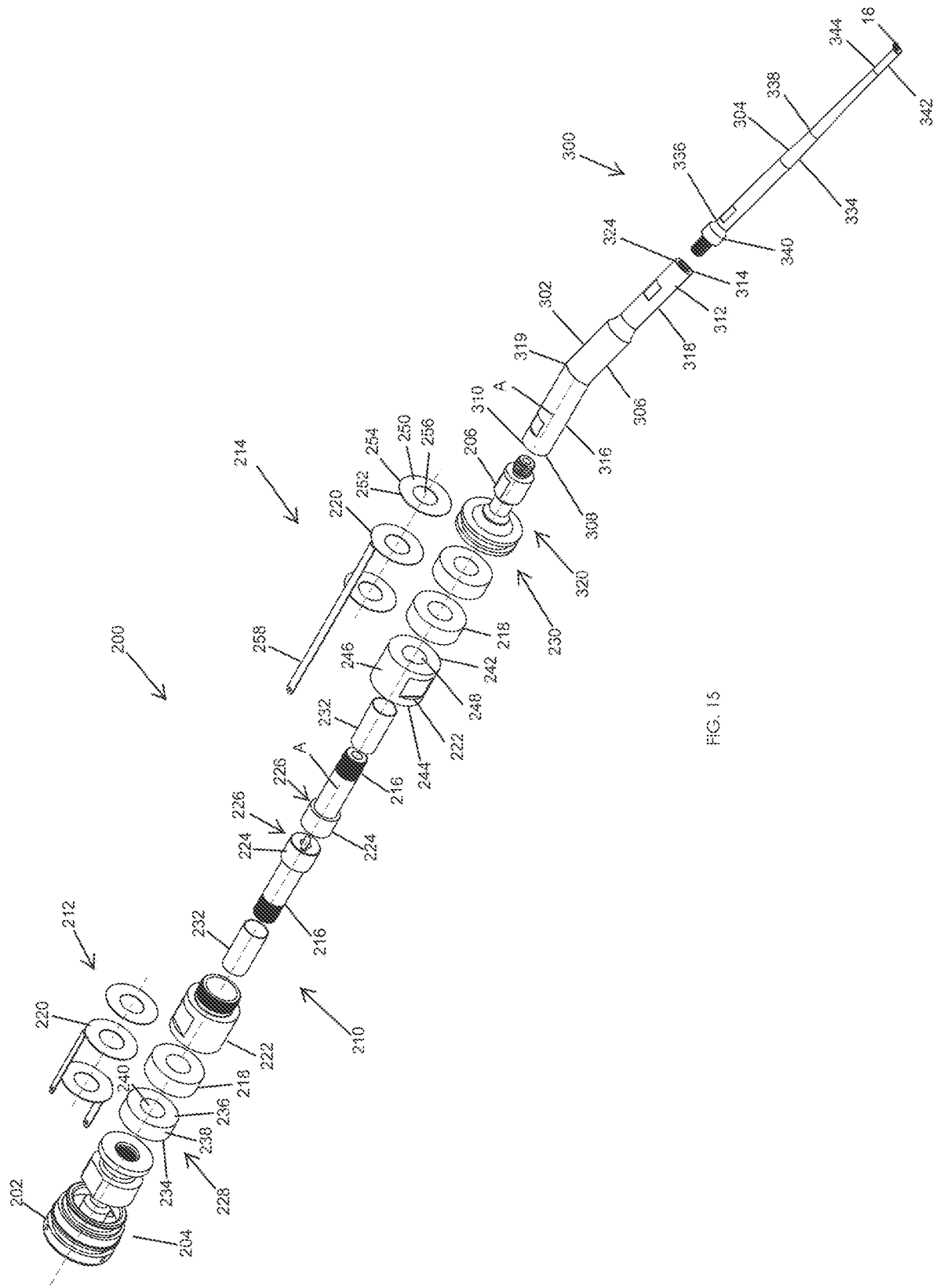
FIG. 15 is an exploded perspective view of a motor and surgical attachment of the ultrasonic surgical handpiece in accordance with an embodiment.

FIG. 15 is an exploded perspective view of a motor 200 and surgical attachment 300 of the ultrasonic surgical handpiece 12 in accordance with an embodiment. In an exemplary embodiment, the surgical attachment 300 includes an angled adaptor 302 and an ultrasonic tool or tip 304 aligned along the central axis A of the handpiece 12. The angled adaptor 302 includes a body 306 having a distal end 308 detachably connected to the motor 200, such as with a threaded bore 310, and a proximal end 312 detachably connected to the tip 304, such as with a threaded bore 314. The body 306 includes a distal portion 316 and a proximal portion 318 offset from each other at angle at a junction 319, such as an angle in the range of about 10°-45°, however, any angle can be used. The angled adaptor 302 may comprise an amplifier interface 320 at the distal end 308, and angled tip interface 324 at the proximal end 312. In one or more embodiments, angled adaptor 302 may comprise angled adaptor bore 330 and a tip bore 332 (FIG. 8). As shown in FIG. 4, the junction 319 is positioned to correlate with a node of the standing wave 100. The correlation of the junction 319 with node 102 increases the amplitude of the standing wave 100 after the junction 319 as it approaches the working plane 18.

In an exemplary embodiment, an ultrasonic tip 304 includes a body 334 having a distal end 336 detachably connected to the proximal end 312 of the angled adaptor 302, such as with a threaded portion, and a proximal end 338 having a working plane 18 configured for engagement of biological tissue. The body 334 may include a plurality of portions having discretely different dimensions to correspond to the nodes 102 and anti-nodes 104 of the standing wave. For example, the body 306 may include a base portion 340 at the distal end 336, a tip portion 342 at the proximal end 338, and a sloped intermediate portion 344 disposed between the base portion 340 and the tip portion 342. A bore 346 extends through the length of body 334 along the center axis A. The ultrasonic tip 304 is configured so that when the handpiece 12 is assembled, the position of the working plane 18 corresponds to one of the anti-nodes 104 of the standing wave 100.

In alternate embodiments of the surgical attachment 300, the angled adaptor 302 and ultrasonic tip 304 may be configured using dimensions that correspond the position of the working plane 18 with an anti-node 104 of the standing wave 100. For example, the ultrasonic tip 304 may have an overall length between distal end 316 and proximal end 318 in a range of about 2.9" inches to about 3.1" inches. The base portion 340 may have a diameter in a range of about 0.2" inches to about 0.3" inches. In alternate embodiments of the surgical attachment 300, the ultrasonic tip 304 may be configured to accomplish various surgical procedures. For example, the ultrasonic tip 304 and in particular the tip portion 342 at the working plane 18 may be configured to engage soft biological tissue, such as, muscular tissue, connective tissue, nervous tissue, epithelial tissue, and the like, or hard biological tissue, such as, bone, enamel, dentin, cementum, and the like.

In one or more embodiments, the angled adaptor 302 and/or the tip 304 may be manufactured from any suitable material, including, but not limited to, polymers, metals, metal alloys, any combination thereof. For example, angled adaptor 302 and/or the tip 304 may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, angled adaptor 302 and/or the tip 304 may be manufactured from an underdamped material, a material having a Q factor greater than 0.5, a metal alloy in an annealed condition, a titanium alloy in an annealed condition, or from Ti-6Al-4V extra-low interstitials in an annealed condition.

FIG. 16 is a side view of the motor 200. FIG. 17 is a cross-section view of the motor 200 taken along section B-B shown in FIG. 10. FIG. 18 is a cross-section view of the motor 200 taken along section C-C shown in FIG. 16. In an exemplary embodiment, the motor 200 includes a connector block 202 at a distal end 204, an amplifier 206 at a proximal end 208, and a transducer assembly 210 disposed between the connector block 202 and the amplifier 206. The connector block 202, transducer assembly 210, and amplifier 206 are aligned along a central axis A of the handpiece 12 and configured for operative connection to the power source 24 via the connection assembly 16 (FIG. 1).

The transducer assembly 210 includes a first stack 212 and a second stack 214 aligned along the center axis A in opposition to each other (FIG. 14). Each stack 212, 214, includes a shaft or bolt 216 configured to couple with a plurality of torsional transducers 218, a set of electrodes 220, and an inert ring 222. For example, the shaft 216 may include a raised collar 224 at a proximal end 226 to abut with the inert ring 222 with a pair of torsional transducers 218 adjacent the inert ring 222. A distal end 228 of the first stack 212 is connected to the connector block 202, and a distal end 230 of the second stack 214 is connected to amplifier 206. A set of three electrodes 220 are disposed between the components and operatively connected to the control system 14 via the electrical connection 30 of the connection assembly 16 (FIG. 9). An insulator sleeve 232 is disposed between the shaft 216, the torsional transducers 218, the electrodes 220, and the inert ring 222 to provide electrical insulation between the components. For example, the insulator 232 may be a generally cylindrical sleeve comprised of any suitable electrically insulating material, such as a thermoplastic polymer material. When assembled, the transducer assembly is placed under a predetermined amount of pre-stress to provide for proper interfacing between components. For example, the transducer assembly 210 is placed under a pre-stress in a range of about 1500-2500 psi. In alternate embodiments, the transducer assembly 210 may include any number of stacks of torsional transducers, including a single stack.

In the illustrated embodiment, each torsional transducer 218 is piezoelectric ring having a distal end surface 234, and proximal end surface 236, a generally annular outer surface 238, and a bore 240. The end surfaces 234, 236 may be generally smooth to increase the acoustic contact between transducers 218 when assembled. For example, the end surfaces 234, 236 may be absent of any coatings and polished to a surface roughness in a range of about 2 Ra to 6 Ra. In alternate embodiments, each ring may include a coating (not shown) on one or more of the surfaces with a predetermined thickness. The coating may be manufactured from an electrically conductive material, such as, aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, and the like.

The dimensions of the transducer 218 are predetermined to achieve the proper piezoelectrical effect. For example, the transducer 218 may have a thickness of about 0.145 to 0.215 inches. However, alternate embodiments may have a thickness of less than 0.145 inches or greater than 0.215 inches. For example, the transducer 218 may have an outer diameter of about 0.465 to 0.655 inches. However, alternate embodiments of may have an outer diameter of less than 0.465 inches or greater than 0.655 inches. For example, the bore 240 of the transducer 218 may have a diameter of about 0.175 to 0.375 inches. However, alternate embodiments may have a diameter of less than 0.175 inches or greater than 0.375 inches.

In an exemplary embodiment, one or more of the torsional transducers 218 may be manufactured from a piezoelectric ceramic material, such as, perovskite material, a lead zirconate titanate ("PZT") material, piezoxide material, a PXE 5 grade material, a PXE 52 grade material, a PXE 59 grade material, a PXE 21 grade material, a PXE 41 grade material, a PXE 42 grade material, a PXE 43 grade material, a PXE 71 grade material, and the like. Alternatively, each transducer may be manufactured from a material having a crystal structure with no center of symmetry, such as, a perovskite crystal structure. In one or more embodiments, each torsional transducer 218 may be manufactured from a material having a tetragonal crystal lattice elementary cell below the material's Curie temperature, such as, a cubic crystal lattice elementary cell above the material's Curie temperature.

In an exemplary embodiment, the inert ring 222 includes a distal end surface 242, and proximal end surface 244, a generally annular outer surface 246, and a bore 248. The dimensions and materials of the transducer 218 are predetermined to achieve the proper configuration of the standing wave 100 along the central axis A, and correspondingly, the position of the nodes 102 and anti-nodes 104. For example, the inert ring 222 may have a thickness of about 0.265 to 0.385 inches. However, alternate embodiments may have a thickness of less than 0.265 inches or greater than 0.385 inches. For example, the inert ring 222 may have an outer diameter of about 0.465 to 0.655 inches. However, alternate embodiments of may have an outer diameter of less than 0.465 inches or greater than 0.655 inches. For example, the bore 248 of the inert ring 222 may have a diameter of about 0.175 to 0.375 inches. However, alternate embodiments may have a diameter of less than 0.175 inches or greater than 0.375 inches.

In one or more embodiments, the inert ring 222 may be manufactured from any suitable material, including but not limited to, polymers, metals, metal alloys, etc., or from any combination of suitable materials. For example, the inert ring 222 may be manufactured from may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, the inert ring 222 may be manufactured from an underdamped material, a material having a Q factor greater than 0.5, a metal alloy in an annealed condition, a titanium alloy in an annealed condition, or from Ti-6Al-4V extra-low interstitials in an annealed condition.

In an exemplary embodiment, each electrode 220 is generally ring-shaped and includes a distal end surface 250, and proximal end surface 252, a generally annular outer surface 254, and a bore 256. One or more of the electrodes may include leads 258 that operatively connect to the control system 14 via the electrical connection 30 of the connection assembly 16 (FIG. 9). The dimensions of the transducer 218 are predetermined to achieve the proper connection between components. For example, the electrode 220 may have a thickness of about 0.700 to 0.900 inches. However, alternate embodiments may have a thickness of less than 0.700 inches or greater than 0.900 inches. For example, the electrode 220 may have an outer diameter of about 0.465 to 0.655 inches. However, alternate embodiments of may have an outer diameter of less than 0.465 inches or greater than 0.655 inches. For example, the bore 256 of the electrode 220 may have a diameter of about 0.175 to 0.375 inches. However, alternate embodiments may have a diameter of less than 0.175 inches or greater than 0.375 inches. One or more of the electrodes 220 may be manufactured from aluminum, an aluminum alloy, silver, a silver alloy, copper, a copper alloy, gold, a gold alloy, platinum, a platinum alloy, tin, a tin alloy, palladium, a palladium alloy, nickel, a nickel alloy, beryllium, a beryllium alloy, tungsten, a tungsten alloy, a steel, chromium, a chromium alloy, titanium, a titanium alloy, and the like.

In an exemplary embodiment, the connector block 202 is a generally cylindrical component having a distal end 260 configured to detachably connect with the connection assembly 16 and a proximal end 262 configured to couple with the transducer assembly 210. The outer surfaces 264 of the connector block 202 are configured to receive O-rings that form a hermetic seal with the housing 110 (FIG. 13). An aspiration bore 266 extends through the connector block 202 having an inlet 268 for coupling with the aspiration barb 82 at the distal end 260, and an outlet 270 for coupling with a bore 290 of transducer assembly 210 at the proximal end 262. An irrigation bore 272 extends through the connector block 202 having an inlet 274 for coupling with the irrigation barb 52 at the distal end 260, and an outlet 276 for coupling with the coupling with the irrigation channels 122 at the proximal end 262. The dimensions of the transducer 218 are predetermined to achieve the proper configuration of the standing wave 100, and correspondingly, the position of the nodes 102 and anti-nodes 104.

In one or more embodiments, the connector block 202 may be manufactured from any suitable material, including but not limited to, polymers, metals, metal alloys, etc., or from any combination of suitable materials. For example, the connector block 202 may be manufactured from may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, the connector block 202 may be manufactured from an underdamped material, a material having a Q factor greater than 0.5, a metal alloy in an annealed condition, a titanium alloy in an annealed condition, or from Ti-6Al-4V extra-low interstitials in an annealed condition.

In an exemplary embodiment, the amplifier 206 is a generally cylindrical component having a proximal end 284 configured to detachably connect with the surgical attachment 300 and a distal end 286 configured to couple with the transducer assembly 210 (FIG. 13). The dimensions of the amplifier 206 are predetermined to achieve the proper configuration of the standing wave 100, and correspondingly, the position of the nodes 102 and anti-nodes 104.

In one or more embodiments, the amplifier 206 may be manufactured from any suitable material, including but not limited to, polymers, metals, metal alloys, etc., or from any combination of suitable materials. For example, the amplifier 206 may be manufactured from may be manufactured from titanium, a titanium alloy, aluminum, an aluminum alloy, copper, a copper alloy, iron, an iron alloy, nickel, a nickel alloy, silver, a silver alloy, cobalt, a cobalt alloy, tin, a tin alloy, gold, a gold alloy, tungsten, a tungsten alloy, beryllium, a beryllium alloy, platinum, a platinum alloy, chromium, a chromium alloy, lead, a lead alloy, palladium, a palladium alloy, zinc, a zinc alloy, rhodium, a rhodium alloy, niobium, a niobium alloy, vanadium, a vanadium alloy, manganese, a manganese alloy, indium, and indium alloy, tantalum, a tantalum alloy, molybdenum, a molybdenum alloy, cadmium, a cadmium alloy, thallium, a thallium alloy, ruthenium, a ruthenium alloy, iridium, an iridium alloy, gallium, a gallium alloy, osmium, an osmium alloy, rhenium, a rhenium alloy, stainless steel, a brass, a bronze, a duralumin, or a nitinol. Illustratively, the amplifier 206 may be manufactured from an underdamped material, a material having a Q factor greater than 0.5, a metal alloy in an annealed condition, a titanium alloy in an annealed condition, or from Ti-6Al-4V extra-low interstitials in an annealed condition.

Figure 19:
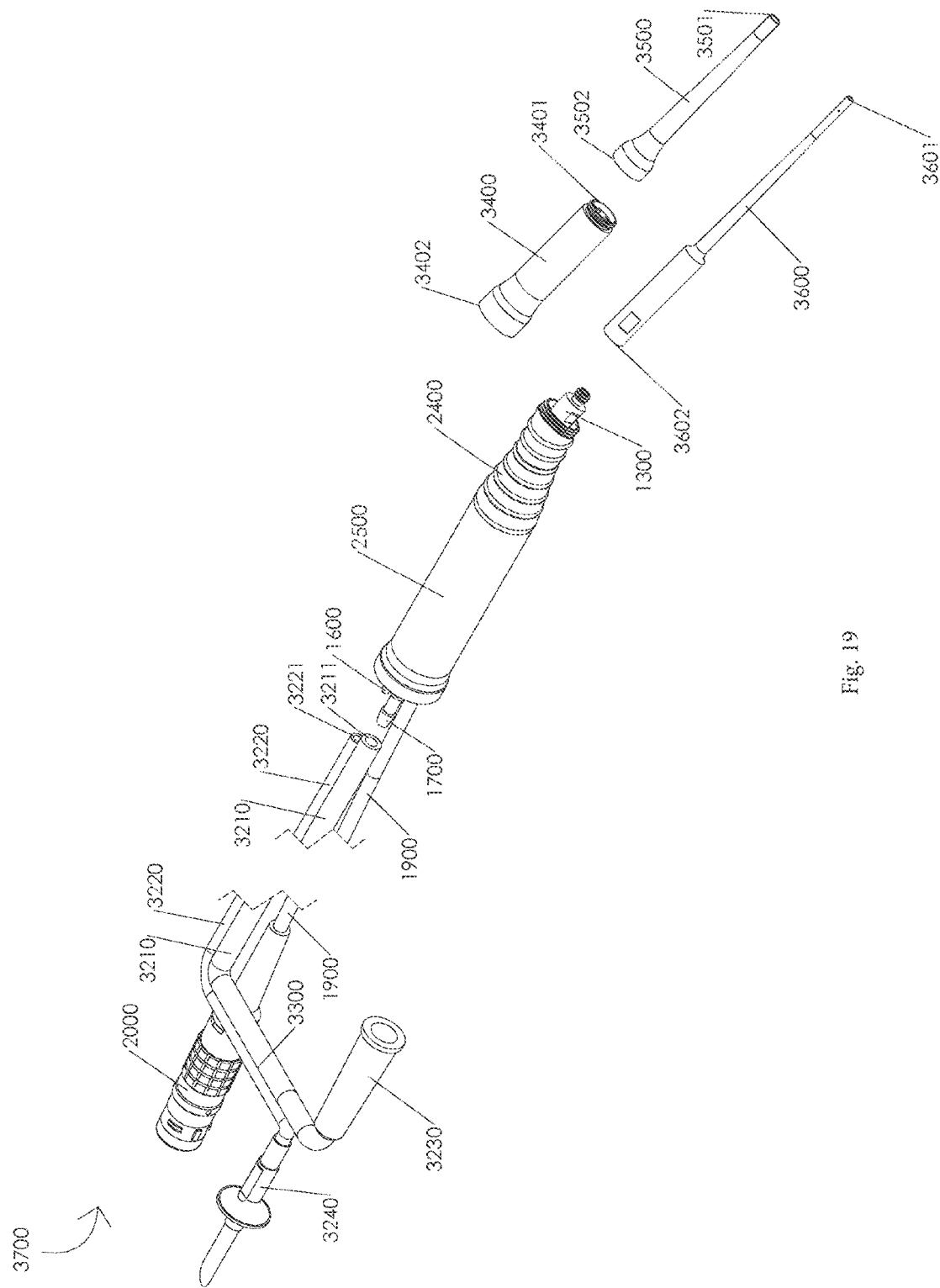
FIG. 19 is an exploded view of an alternate embodiment of an ultrasonic handpiece assembly

FIG. 19 is an exploded view of an alternate embodiment of an ultrasonic handpiece assembly 3700. In one or more embodiments, an ultrasonic handpiece assembly 3700 may comprise an assembled handpiece 3100, an assembled tubing set 3300, a proximal irrigation sleeve 3400, a distal irrigation sleeve 3500, and an ultrasonic tip 3600.

Figure 20:
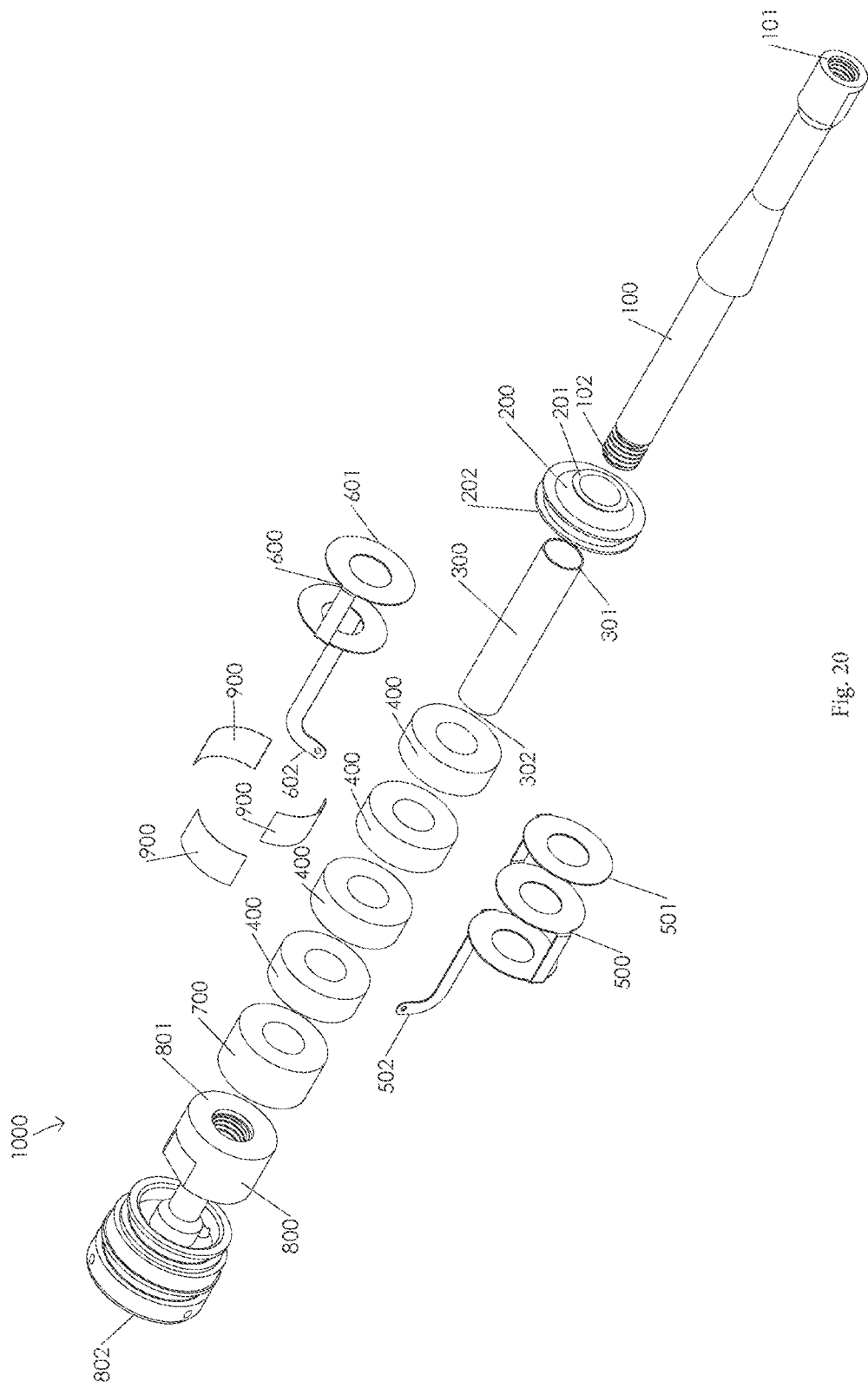
FIG. 20 is an exploded view of an alternate embodiment of a transducer assembly.

FIG. 20 is an exploded view of an alternate embodiment of a transducer assembly 1000.

In one or more embodiments, a transducer assembly 1000 may comprise an amplifier 100, a flange 200, an amplifier sleeve 300, a first piezoelectric ring 400, a second piezoelectric ring 400, a third piezoelectric ring 400, a fourth piezoelectric ring 400, an outer electrode stack 500, an inner electrode stack 600, an inert ring 700, a connector block 800, a first electrical insulator 900, a second electrical insulator 900, and a third electrical insulator 900.

Illustratively, a geometry of outer electrode stack 500 may be configured for a transducer assembly 1000, e.g., by folding first medial electrical conductor 505 into a plane normal to first lateral electrical conductor 510. In one or more embodiments, a geometry of outer electrode stack 500 may be configured for a transducer assembly 1000, e.g., by folding third medial electrical conductor 515 into a plane normal to first lateral electrical conductor 510. Illustratively, a geometry of outer electrode stack 500 may be configured for a transducer assembly 1000, e.g., by folding third medial electrical conductor 515 into a plane parallel to first medial electrical conductor 505. In one or more embodiments, a geometry of outer electrode stack 500 may be configured for a transducer assembly 1000, e.g., by folding third lateral electrical conductor 520 into a plane nor-mal to third medial electrical conductor 515. Illustratively, a geometry of outer electrode stack 500 may be configured for a transducer assembly 1000, e.g., by folding third lateral electrical conductor 520 into a plane normal to first medial electrical conductor 505. In one or more embodiments, a geometry of outer electrode stack 500 may be configured for a transducer assembly 1000, e.g., by folding third lateral electrical conductor 520 into a plane parallel to first lateral electrical conductor 510. Illustratively, a geometry of outer electrode stack 500 may be configured for a transducer assembly 1000, e.g., by folding fifth medial electrical conductor 525 into a plane normal to third lateral electrical conductor 520. In one or more embodiments, a geometry of outer electrode stack 500 may be configured for a transducer assembly 1000, e.g., by folding fifth medial electrical conductor 525 into a plane normal to first lateral electrical conductor 510. Illustratively, a geometry of outer electrode stack 500 may be configured for a transducer assembly 1000, e.g., by folding fifth medial electrical conductor 525 into a plane parallel to third medial electrical conductor 515. In one or more embodiments, a geometry of outer electrode stack 500 may be configured for a transducer assembly 1000, e.g., by folding fifth medial electrical conductor 525 into a plane parallel to first medial electrical conductor 505. Illustratively, a geometry of outer electrode stack 500 may be configured for a transducer assembly 1000, e.g., by folding first lead 530 into a plane normal to fifth medial electrical conductor 525. In one or more embodiments, a geometry of outer electrode stack 500 may be configured for a transducer assembly 1000, e.g., by folding first lead 530 into a plane normal to third medial electrical conductor 515. Illustratively, a geometry of outer electrode stack 500 may be configured for a transducer assembly 1000, e.g., by folding first lead 530 into a plane normal to first medial electrical conductor 505. In one or more embodiments, a geometry of outer electrode stack 500 may be configured for a transducer assembly 1000, e.g., by folding first lead 530 into a plane parallel to third lateral electrical conductor 520. Illustratively, a geometry of outer electrode stack 500 may be con-figured for a transducer assembly 1000, e.g., by folding first lead 530 into a plane parallel to first lateral electrical conductor 510. In one or more embodiments, a geometry of outer electrode stack 500 may be configured for a transducer assembly 1000, e.g., by folding first lead 530 into a plane coplanar with first lateral electrical conductor 510.

Illustratively, a geometry of inner electrode stack 600 may be configured for a transducer assembly 1000, e.g., by folding second medial electrical conductor 605 into a plane normal to second lateral electrical conductor 610. In one or more embodiments, a geometry of inner electrode stack 600 may be configured for a transducer assembly 1000, e.g., by folding fourth medical electrical conductor 615 into a plane normal to second lateral electrical conductor 610. Illustratively, a geometry of inner electrode stack 600 may be configured for a transducer assembly 1000, e.g., by folding fourth medical electrical conductor 615 into a plane parallel to second medial electrical conductor 605. In one or more embodiments, a geometry of inner electrode stack 600 may be configured for a transducer assembly 1000, e.g., by folding second lead 620 into a plane normal to fourth medial electrical conductor 610. Illustratively, a geometry of inner electrode stack 600 may be configured for a transducer assembly 1000, e.g., by folding second lead 620 into a plane normal to second medial electrical conductor 605. In one or more embodiments, a geometry of inner electrode stack 600 may be configured for a transducer assembly 1000, e.g., by folding second lead 620 into a plane parallel to second lateral electrical conductor 610.

Figure 21:
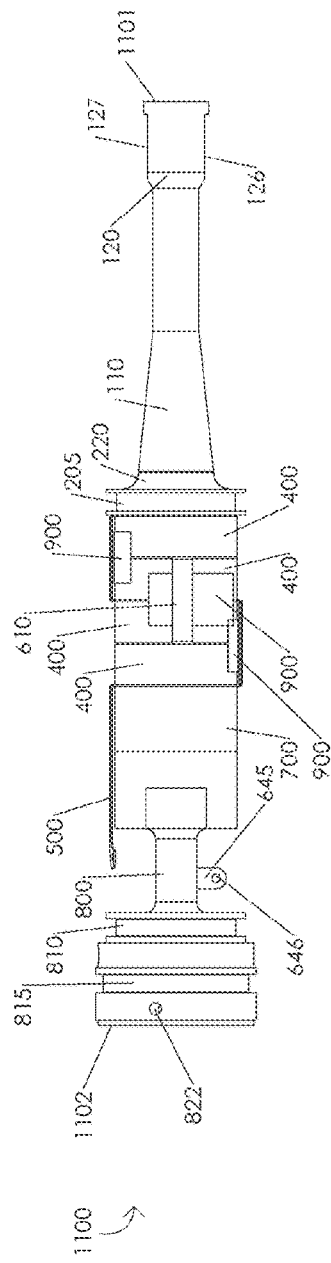
FIG. 21 is a top view of an alternate embodiment of an assembled transducer.
Figure 22:
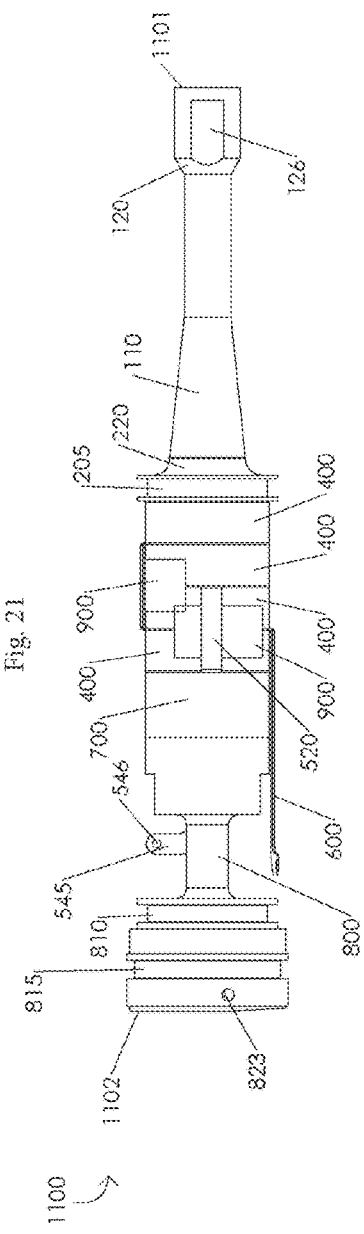
FIG. 22 is a side view of an alternate embodiment of the assembled transducer.
Figure 23:
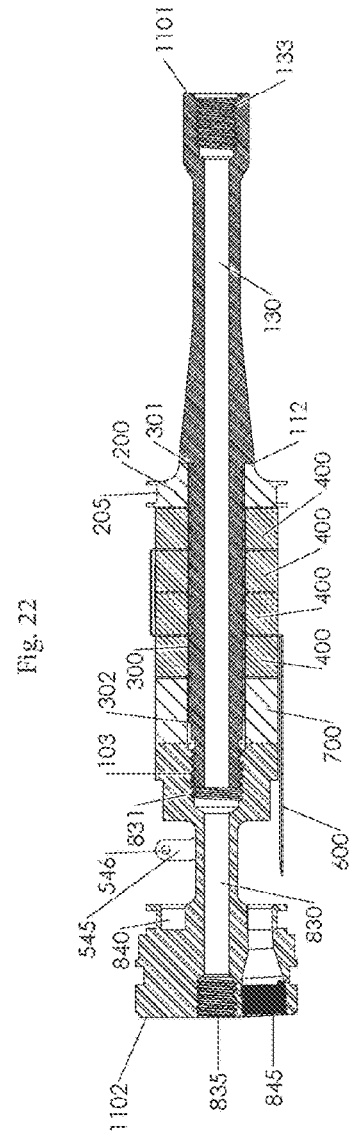
FIG. 23 is a cross-section view of an alternate embodiment of the assembled transducer.

FIGS. 21, 22, and 23 are schematic diagrams illustrating an alternate embodiment of an assembled transducer 1100. FIG. 21 illustrates a top view of the assembled transducer 1100. FIG. 22 illustrates a side view of the assembled transducer 1100. FIG. 23 illustrates a cross-sectional view of the assembled transducer 1100. In one or more embodiments, an assembled transducer 1100 may comprise an assembled transducer distal end 1101 and an assembled transducer proximal end 1102. Illustratively, assembled transducer 1100 may comprise a composite transducer, e.g., assembled transducer 1100 may comprise a mechanically pre-stressed composite transducer.

In one or more embodiments, amplifier sleeve 300 may be disposed over a portion of amplifier 100, e.g., amplifier sleeve 300 may be disposed over proximal base 105. Illustratively, amplifier sleeve 300 may be disposed over a portion of amplifier 100 wherein amplifier sleeve distal end 301 is adjacent to flange interface taper proximal end 112, e.g., amplifier sleeve 300 may be disposed over a portion of amplifier 100 wherein amplifier sleeve distal end 301 abuts flange interface taper proximal end 112. In one or more embodiments, amplifier sleeve 300 may be disposed over a portion of amplifier 100 wherein amplifier sleeve distal end 301 is adjacent to proximal base distal end 106, e.g., amplifier sleeve 300 may be disposed over a portion of amplifier 100 wherein amplifier sleeve distal end 301 abuts proximal base distal end 106. Illustratively, amplifier sleeve 300 may be disposed over a portion of amplifier 100 wherein amplifier sleeve distal end 301 is coplanar with proximal base distal end 106. In one or more embodiments, amplifier sleeve 300 may be disposed over a portion of amplifier 100 wherein amplifier sleeve proximal end 302 is disposed distally of proximal base proximal end 107, e.g., amplifier sleeve 300 may be disposed over a portion of amplifier 100 wherein amplifier sleeve proximal end 302 is disposed distally of amplifier proximal thread 103.

Illustratively, flange 200 may be disposed over a portion of amplifier 100, e.g., flange 200 may be disposed over proximal base 105. In one or more embodiments, flange 200 may be disposed over a portion of amplifier sleeve 300. Illustratively, flange 200 may be disposed over a portion of amplifier 100 and amplifier sleeve 300, e.g., flange 200 may be disposed over a portion of amplifier 100 and amplifier sleeve 300 wherein proximal base 105 and amplifier sleeve 300 are disposed in flange inner bore 230. In one or more embodiments, a portion of amplifier sleeve 300 may be disposed between a portion of amplifier 100 and flange 200, e.g., a portion of amplifier sleeve 300 may be disposed between proximal base 105 and flange 200. Illustratively, flange 200 may be disposed over a portion of amplifier 100 wherein flange distal end 201 is adjacent to flange inter-face taper proximal end 112, e.g., flange 200 may be disposed over a portion of amplifier 100 wherein flange distal end 201 abuts flange interface taper proximal end 112. In one or more embodiments, flange 200 may be disposed over a portion of amplifier 100 wherein flange distal end 201 is adjacent to proximal base distal end 106, e.g., flange 200 may be disposed over a portion of amplifier 100 wherein flange distal end 201 abuts proximal base distal end 106. Illustratively, flange 200 may be disposed over a portion of ampli-fier 100 wherein flange distal end 201 is coplanar with proximal base distal end 106. In one or more embodiments, flange 200 may be disposed over a portion of amplifier sleeve 300 wherein flange distal end 201 is adjacent to amplifier sleeve distal end 301, e.g., flange 200 may be disposed over a portion of amplifier sleeve 300 wherein flange distal end 201 abuts amplifier sleeve distal end 301. Illustratively, flange 200 may be disposed over a portion of amplifier sleeve 300 wherein flange distal end 201 is coplanar with amplifier sleeve distal end 301. In one or more embodiments, flange 200 may be disposed over a portion of amplifier 100 and amplifier sleeve 300 wherein flange distal end 201 is adjacent to proximal base distal end 106 and amplifier sleeve distal end 301, e.g., flange 200 may be disposed over a portion of amplifier 100 and amplifier sleeve 300 wherein flange distal end 201 abuts proximal base distal end 106 and amplifier sleeve distal end 301. Illustratively, flange 200 may be disposed over a portion of amplifier 100 and amplifier sleeve 300 wherein flange distal end 201 is coplanar with proximal base distal end 106 and amplifier sleeve distal end 301.

In one or more embodiments, a portion of outer electrode stack 500 may be dis-posed over a portion of amplifier 100, e.g., first medial electrical conductor 505 may be disposed over a portion of amplifier 100 wherein proximal base 105 is disposed in first medial aperture 506. Illustratively, a portion of outer electrode stack 500 may be dis-posed over a portion of amplifier sleeve 300, e.g., first medial electrical conductor 505 may be disposed over a portion of amplifier sleeve 300 wherein the portion of amplifier sleeve is dis-posed in first medial aperture 506. In one or more embodiments, a portion of outer electrode stack 500 may be disposed over a portion of amplifier sleeve 300 and a portion of amplifier 100 wherein the portion of amplifier sleeve 300 and the portion of amplifier 100 are disposed in first medial aperture 506, e.g., first medial electrical conductor 505 may be disposed over a portion of amplifier sleeve 300 and a portion of amplifier 100 wherein the portion of amplifier sleeve 300 is disposed between the portion of amplifier 100 and first medial electrical conductor 505. Illustratively, a portion of outer electrode stack 500 may be disposed over amplifier sleeve 300 and amplifier 100 wherein first medial electrical conductor 505 is adjacent to flange proximal end 202, e.g., a portion of outer electrode stack 500 may be disposed over amplifier sleeve 300 and amplifier 100 wherein first medial electrical conductor 505 abuts flange proximal end 202.

In one or more embodiments, first piezoelectric ring 400 may be disposed over a portion of amplifier 100, e.g., first piezoelectric ring 400 may be disposed over a portion of amplifier 100 wherein proximal base 105 is disposed in first piezoelectric ring inner bore 411. Illustratively, first piezoelectric ring 400 may be disposed over a portion of amplifier sleeve 300, e.g., first piezoelectric ring 400 may be disposed over a portion of amplifier sleeve 300 wherein the portion of amplifier sleeve 300 is disposed in first piezo-electric ring inner bore 411. In one or more embodiments, first piezoelectric ring 400 may be disposed over a portion of amplifier sleeve 300 and a portion of amplifier 100 wherein the portion of amplifier sleeve 300 and the portion of amplifier 100 are disposed in first piezoelectric ring inner bore 411, e.g., first piezoelectric ring 400 may be disposed over a portion of amplifier sleeve 300 and a portion of amplifier 100 wherein the portion of amplifier sleeve 300 is disposed between the portion of amplifier 100 and first piezoelectric ring 400. Illustratively, first piezoelectric ring 400 may be disposed over amplifier sleeve 300 and amplifier 100 wherein first piezoelectric ring distal end 401 is adjacent to first medial electrical conductor 505, e.g., first piezoelectric ring 400 may be disposed over amplifier sleeve 300 and amplifier 100 wherein first piezoelectric ring distal end 401 abuts first medial electrical conductor 505. In one or more embodiments, first piezoelectric ring 400 may be disposed over amplifier sleeve 300 and amplifier 100 wherein first medial electrical conductor 505 is disposed between first piezoelectric ring 400 and flange 200, e.g., first piezoelectric ring 400 may be disposed over amplifier sleeve 300 and amplifier 100 wherein first medial electrical conductor 505 is disposed between first piezoelectric ring distal end 401 and flange proximal end 202.

Illustratively, a portion of inner electrode stack 600 may be disposed over a portion of amplifier 100, e.g., second medial electrical conductor 605 may be disposed over a portion of amplifier 100 wherein proximal base 105 is disposed in second medial aperture 606. In one or more embodiments, a portion of inner electrode stack 600 may be dis-posed over a portion of amplifier sleeve 300, e.g., second medial electrical conductor 605 may be disposed over a portion of amplifier sleeve 300 wherein the portion of amplifier sleeve 300 is disposed in second medial aperture 606. Illustratively, a portion of inner electrode stack 600 may be disposed over a portion of amplifier sleeve 300 and a portion of amplifier 100 wherein the portion of amplifier sleeve 300 and the portion of amplifier 100 are disposed in second medial aperture 606, e.g., second medial electrical conductor 605 may be disposed over a portion of amplifier sleeve 300 and a portion of amplifier 100 wherein the portion of amplifier sleeve 300 is disposed between the portion of amplifier 100 and second medial electrical conductor 605. In one or more embodiments, a portion of inner electrode stack 600 may be disposed over amplifier sleeve 300 and amplifier 100 wherein second medial electrical conductor 605 is adjacent to first piezoelectric ring proximal end 402, e.g., a portion of inner electrode stack 600 may be disposed over amplifier sleeve 300 and amplifier 100 wherein second medial electrical conductor 605 abuts first piezoelectric ring proximal end 402. Illustratively, second medial electrical conductor 605 may be disposed over amplifier sleeve 300 and amplifier 100 wherein first piezoelectric ring 400 is disposed between second medial electrical conductor 605 and first medial electrical conductor 505, e.g., second medial electrical conductor 605 may be disposed over amplifier sleeve 300 and amplifier 100 wherein first piezoelectric ring distal end 401 abuts first medial electrical conductor 505 and wherein first piezoelectric ring proximal end 402 abuts second medial electrical conductor 605.

In one or more embodiments, second piezoelectric ring 400 may be disposed over a portion of amplifier 100, e.g., second piezoelectric ring 400 may be disposed over a portion of amplifier 100 wherein proximal base 105 is disposed in second piezoelectric ring inner bore 411. Illustratively, second piezoelectric ring 400 may be disposed over a portion of amplifier sleeve 300, e.g., second piezoelectric ring 400 may be disposed over a portion of amplifier sleeve 300 wherein the portion of amplifier sleeve 300 is disposed in second piezoelectric ring inner bore 411. In one or more embodiments, second piezoelectric ring 400 may be disposed over a portion of amplifier sleeve 300 and a portion of amplifier 100 wherein the portion of amplifier sleeve 300 and the portion of amplifier 100 are disposed in second piezoelectric ring inner bore 411, e.g., second piezoelectric ring 400 may be disposed over a portion of amplifier sleeve 300 and a portion of amplifier 100 wherein the portion of amplifier sleeve 300 is disposed between the portion of amplifier 100 and second piezoelectric ring 400. Illustratively, second piezoelectric ring 400 may be disposed over amplifier sleeve 300 and amplifier 100 wherein second piezoelectric ring proximal end 402 is adjacent to second medial electrical conductor 605, e.g., second piezoelectric ring 400 may be disposed over amplifier sleeve 300 and amplifier 100 wherein second piezoelectric ring proximal end 402 abuts second medial electrical conductor 605. In one or more embodiments, second piezoelectric ring 400 may be disposed over amplifier sleeve 300 and amplifier 100 wherein second medial electrical conductor 605 is dis-posed between first piezoelectric ring 400 and second piezoelectric ring 400, e.g., second piezoelectric ring 400 may be dis-posed over amplifier sleeve 300 and amplifier 100 wherein second medial electrical conductor 605 is disposed between first piezoelectric ring proximal end 402 and second piezoelectric ring proximal end 402.

Illustratively, a portion of outer electrode stack 500 may be disposed over a portion of amplifier 100, e.g., third medial electrical conductor 515 may be disposed over a portion of amplifier 100 wherein proximal base 105 is disposed in third medial aperture 516. In one or more embodiments, a portion of outer electrode stack 500 may be dis-posed over a portion of amplifier sleeve 300, e.g., third medial electrical conductor 515 may be disposed over a portion of amplifier sleeve 300 wherein the portion of amplifier sleeve 300 is disposed in third medial aperture 516. Illustratively, a portion of outer electrode stack 500 may be disposed over a portion of amplifier sleeve 300 and a portion of amplifier 100 wherein the portion of amplifier sleeve 300 and the portion of amplifier 100 are disposed in third medial aperture 516, e.g., third medial electrical conductor 515 may be disposed over a portion of amplifier sleeve 300 and a portion of amplifier 100 wherein the portion of amplifier sleeve 300 is disposed between the portion of amplifier 100 and third medial electrical conductor 515. In one or more embodiments, a portion of outer electrode stack 500 may be disposed over amplifier sleeve 300 and amplifier 100 wherein third medial electrical conductor 515 is adjacent to second piezoelectric ring distal end 401, e.g., a portion of outer electrode stack 500 may be disposed over amplifier sleeve 300 and amplifier 100 wherein third medial electrical conductor 515 abuts second piezoelectric ring distal end 401. Illustratively, third medial electrical conductor 515 may be disposed over amplifier sleeve 300 and amplifier 100 wherein second piezoelectric ring 400 is disposed between second medial electrical conductor 605 and third medial electrical conductor 515, e.g., third medial electrical conductor 515 may be disposed over amplifier sleeve 300 and amplifier 100 wherein second piezoelectric ring distal end 401 abuts third medial electrical conductor 515 and wherein second piezoelectric ring proximal end 402 abuts second medial electrical conductor 605.

In one or more embodiments, third piezoelectric ring 400 may be disposed over a portion of amplifier 100, e.g., third piezoelectric ring 400 may be disposed over a portion of amplifier 100 wherein proximal base 105 is disposed in third piezoelectric ring inner bore 411. Illustratively, third piezoelectric ring 400 may be disposed over a portion of amplifier sleeve 300, e.g., third piezoelectric ring 400 may be dis-posed over a portion of amplifier sleeve 300 wherein the portion of amplifier sleeve 300 is disposed in third piezoelectric ring inner bore 411. In one or more embodiments, third piezoelectric ring 400 may be disposed over a portion of amplifier sleeve 300 and a portion of amplifier 100 wherein the portion of amplifier sleeve 300 and the portion of amplifier 100 are disposed in third piezoelectric ring inner bore 411, e.g., third piezoelectric ring 400 may be dis-posed over a portion of amplifier sleeve 300 and a portion of amplifier 100 wherein the portion of amplifier sleeve 300 is disposed between the portion of amplifier 100 and third piezoelectric ring 400. Illustratively, third piezoelectric ring 400 may be disposed over amplifier sleeve 300 and amplifier 100 wherein third piezoelectric ring distal end 401 is adjacent to third medial electrical conductor 515, e.g., third piezoelectric ring 400 may be disposed over amplifier sleeve 300 and amplifier 100 wherein third piezoelectric ring distal end 401 abuts third medial electrical conductor 515. In one or more embodiments, third piezoelectric ring 400 may be disposed over amplifier sleeve 300 and amplifier 100 wherein third medial electrical conductor 515 is disposed between second piezoelectric ring 400 and third piezoelectric ring 400, e.g., third piezoelectric ring 400 may be dis-posed over amplifier sleeve 300 and amplifier 100 wherein third medial electrical conductor 515 is disposed between second piezoelectric ring distal end 401 and third piezoelectric ring distal end 401.

Illustratively, a portion of inner electrode stack 600 may be disposed over a portion of amplifier 100, e.g., fourth medial electrical conductor 615 may be disposed over a portion of amplifier 100 wherein proximal base 105 is disposed in fourth medial aperture 616. In one or more embodiments, a portion of inner electrode stack 600 may be dis-posed over a portion of amplifier sleeve 300, e.g., fourth medial electrical conductor 615 may be disposed over a portion of amplifier sleeve 300 wherein the portion of amplifier sleeve 300 is disposed in fourth medial aperture 616. Illustratively, a portion of inner electrode stack 600 may be disposed over a portion of amplifier sleeve 300 and a portion of amplifier 100 wherein the portion of amplifier sleeve 300 and the portion of amplifier 100 are disposed in fourth medial aperture 616, e.g., fourth medial electrical conductor 615 may be disposed over a portion of amplifier sleeve 300 and a portion of amplifier 100 wherein the portion of amplifier sleeve 300 is disposed between the portion of amplifier 100 and fourth medial electrical conductor 615. In one or more embodiments, a portion of inner electrode stack 600 may be disposed over amplifier sleeve 300 and amplifier 100 wherein fourth medial electrical conductor 615 is adjacent to third piezoelectric ring proximal end 402, e.g., a portion of inner electrode stack 600 may be disposed over amplifier sleeve 300 and amplifier 100 wherein fourth medial electrical conductor 615 abuts third piezoelectric ring proximal end 402. Illustratively, fourth medial electrical conductor 615 may be disposed over amplifier sleeve 300 and amplifier 100 wherein third piezoelectric ring 400 is disposed between fourth medial electrical conductor 615 and third medial electrical conductor 515, e.g., fourth medial electrical conductor 615 may be disposed over amplifier sleeve 300 and amplifier 100 wherein third piezoelectric ring distal end 401 abuts third medial electrical conductor 515 and wherein third piezoelectric ring proximal end 402 abuts fourth medial electrical conductor 615.

In one or more embodiments, fourth piezoelectric ring 400 may be disposed over a portion of amplifier 100, e.g., fourth piezoelectric ring 400 may be disposed over a portion of amplifier 100 wherein proximal base 105 is disposed in fourth piezoelectric ring inner bore 411. Illustratively, fourth piezoelectric ring 400 may be disposed over a portion of amplifier sleeve 300, e.g., fourth piezoelectric ring 400 may be disposed over a portion of amplifier sleeve 300 wherein the portion of amplifier sleeve 300 is disposed in fourth piezoelectric ring inner bore 411. In one or more embodiments, fourth piezoelectric ring 400 may be disposed over a portion of amplifier sleeve 300 and a portion of amplifier 100 wherein the portion of amplifier sleeve 300 and the portion of amplifier 100 are disposed in fourth piezoelectric ring inner bore 411, e.g., fourth piezoelectric ring 400 may be disposed over a portion of amplifier sleeve 300 and a portion of amplifier 100 wherein the portion of amplifier sleeve 300 is disposed between the portion of amplifier 100 and fourth piezoelectric ring 400. Illustratively, fourth piezoelectric ring 400 may be disposed over amplifier sleeve 300 and amplifier 100 wherein fourth piezoelectric ring proximal end 402 is adjacent to fourth medial electrical conductor 615, e.g., fourth piezo-electric ring 400 may be disposed over amplifier sleeve 300 and amplifier 100 wherein fourth piezoelectric ring proximal end 402 abuts fourth medial electrical conductor 615. In one or more embodiments, fourth piezoelectric ring 400 may be disposed over amplifier sleeve 300 and amplifier 100 wherein fourth medial electrical conductor 615 is dis-posed between fourth piezoelectric ring 400 and third piezoelectric ring 400, e.g., fourth piezoelectric ring 400 may be disposed over amplifier sleeve 300 and amplifier 100 wherein fourth medial electrical conductor 615 is disposed between third piezoelectric ring proximal end 402 and fourth piezoelectric ring proximal end 402.

Illustratively, a portion of outer electrode stack 500 may be disposed over a portion of amplifier 100, e.g., fifth medial electrical conductor 525 may be disposed over a portion of amplifier 100 wherein proximal base 105 is disposed in fifth medial aperture 526. In one or more embodiments, a portion of outer electrode stack 500 may be dis-posed over a portion of amplifier sleeve 300, e.g., fifth medial electrical conductor 525 may be disposed over a portion of amplifier sleeve 300 wherein the portion of amplifier sleeve 300 is disposed in fifth medial aperture 526. Illustratively, a portion of outer electrode stack 500 may be disposed over a portion of amplifier sleeve 300 and a portion of amplifier 100 wherein the portion of amplifier sleeve 300 and the portion of amplifier 100 are disposed in fifth medial aperture 526, e.g., fifth medial electrical conductor 525 may be disposed over a portion of amplifier sleeve 300 and a portion of amplifier 100 wherein the portion of amplifier sleeve 300 is disposed between the portion of amplifier 100 and fifth medial electrical conductor 525. In one or more embodiments, a portion of outer electrode stack 500 may be disposed over amplifier sleeve 300 and amplifier 100 wherein fifth medial electrical conductor 525 is adjacent to fourth piezoelectric ring distal end 401, e.g., a portion of outer electrode stack 500 may be disposed over amplifier sleeve 300 and amplifier 100 wherein fifth medial electrical conductor 525 abuts fourth piezoelectric ring distal end 401. Illustratively, fifth medial electrical conductor 525 may be disposed over amplifier sleeve 300 and amplifier 100 wherein fourth piezoelectric ring 400 is disposed between fourth medial electrical conductor 615 and fifth medial electrical conductor 525, e.g., fifth medial electrical conductor 525 may be disposed over amplifier sleeve 300 and amplifier 100 wherein fourth piezoelectric ring distal end 401 abuts fifth medial electrical conductor 525 and wherein fourth piezoelectric ring proximal end 402 abuts fourth medial electrical conductor 615.

In one or more embodiments, inert ring 700 may be disposed over a portion of amplifier 100, e.g., inert ring 700 may be disposed over a portion of amplifier 100 wherein proximal base 105 is disposed in inert ring inner bore 711. Illustratively, inert ring 700 may be disposed over a portion of amplifier sleeve 300, e.g., inert ring 700 may be dis-posed over a portion of amplifier sleeve 300 wherein the portion of amplifier sleeve 300 is disposed in inert ring inner bore 711. In one or more embodiments, inert ring 700 may be disposed over a portion of amplifier sleeve 300 and a portion of amplifier 100 wherein the portion of amplifier sleeve 300 and the portion of amplifier 100 are disposed in inert ring inner bore 711, e.g., inert ring 700 may be disposed over a portion of amplifier sleeve 300 and a portion of amplifier 100 wherein the portion of amplifier sleeve 300 is disposed between the portion of amplifier 100 and inert ring 700. Illustratively, inert ring 700 may be disposed over amplifier sleeve 300 and amplifier 100 wherein amplifier sleeve proximal end 302 is disposed in inert ring inner bore 711, e.g., inert ring 700 may be disposed over amplifier sleeve 300 and amplifier 100 wherein proximal base proximal end 107 is dis-posed in inert ring inner bore 711. In one or more embodiments, inert ring 700 may be disposed over amplifier sleeve 300 and amplifier 100 wherein a portion of amplifier proximal undercut 104 is disposed in inert ring inner bore 711. Illustratively, inert ring 700 may be disposed over amplifier sleeve 300 and amplifier 100 wherein inert ring distal end 701 is adjacent to fifth medial electrical conductor 525, e.g., inert ring 700 may be dis-posed over amplifier sleeve 300 and amplifier 100 wherein inert ring distal end 701 abuts fifth medial electrical conductor 525. In one or more embodiments, inert ring 700 may be disposed over amplifier sleeve 300 and amplifier 100 wherein fifth medial electrical conductor 525 is disposed between fourth piezoelectric ring 400 and inert ring 700, e.g., inert ring 700 may be disposed over amplifier sleeve 300 and amplifier 100 wherein fifth medial electrical conductor 525 is disposed between fourth piezoelectric ring distal end 401 and inert ring distal end 701.

Illustratively, first electrical insulator 900 may be disposed between first lateral electrical conductor 510 and first piezoelectric ring 400, e.g., first electrical insulator 900 may be configured to electrically isolate first lateral electrical conductor 510 and first piezoelectric ring 400. In one or more embodiments, first electrical insulator 900 may be disposed between first lateral electrical conductor 510 and second medial electrical conductor 605, e.g., first electrical insulator 900 may be configured to electrically isolate first lateral electrical conductor 510 and second medial electrical conductor 605. Illustratively, first electrical insulator 900 may be disposed between first lateral electrical conductor 510 and second piezoelectric ring 400, e.g., first electrical insulator 900 may be configured to electrically isolate first lateral electrical conductor 510 and second piezoelectric ring 400.

In one or more embodiments, second electrical insulator 900 may be disposed between second lateral electrical conductor 610 and second piezoelectric ring 400, e.g., second electrical insulator 900 may be configured to electrically isolate second lateral electrical conductor 610 and second piezoelectric ring 400. Illustratively, second electrical insulator 900 may be disposed between second lateral electrical conductor 610 third medial electrical conductor 515, e.g., second electrical insulator 900 may be configured to electrically isolate second lateral electrical conductor 610 and third medial electrical conductor 515. In one or more embodiments, second electrical insulator 900 may be disposed between second lateral electrical conductor 610 and third piezoelectric ring 400, e.g., second electrical insulator 900 may be configured to electrically isolate second lateral electrical conductor 610 and third piezoelectric ring 400.

Illustratively, third electrical insulator 900 may be disposed between third lateral electrical conductor 520 and third piezoelectric ring 400, e.g., third electrical insulator 900 may be configured to electrically isolate third lateral electrical conductor 520 and third piezoelectric ring 400. In one or more embodiments, third electrical insulator 900 may be disposed between third lateral electrical conductor 520 and fourth medial electrical conductor 615, e.g., third electrical insulator 900 may be configured to electrically isolate third lateral electrical conductor 520 and fourth medial electrical conductor 615. Illustratively, third electrical insulator 900 may be disposed between third lateral electrical conductor 520 and fourth piezoelectric ring 400, e.g., third electrical insulator 900 may be configured to electrically isolate third lateral electrical conductor 520 and fourth piezoelectric ring 400.

In one or more embodiments, a portion of connector block 800 may be disposed over a portion of amplifier 100, e.g., a portion of connector block 800 may be disposed over amplifier proximal end 102. Illustratively, a portion of connector block 800 may be disposed over a portion of amplifier 100 wherein a portion of connector block distal undercut 832 may be disposed over a portion of amplifier proximal undercut 104. In one or more embodiments, a portion of connector block 800 may be disposed over a portion of amplifier 100 wherein amplifier proximal end 102 may be disposed in amplifier housing 833, e.g., a portion of connector block 800 may be disposed over a portion of amplifier 100 wherein amplifier proximal end 102 may be disposed in amplifier housing taper 834. Illustratively, a portion of connector block 800 may be disposed over amplifier proximal thread 103, e.g., connector block distal thread 831 may be disposed over amplifier proximal thread 103. In one or more embodiments, amplifier proximal thread 103 may comprise an external thread and connector block distal thread 831 may comprise an internal thread, e.g., connector block distal thread 831 and amplifier proximal thread 103 may be configured to convert a torque into a linear force. Illustratively, amplifier proximal thread 103 may comprise an internal thread and connector block distal thread 831 may comprise an external thread, e.g., amplifier proximal thread 103 and connector block distal thread 831 may be configured to convert a torque into a linear force. In one or more embodiments, a portion of amplifier 100 may be disposed in a portion of connector block 800 wherein a portion of connector block 800 is adjacent to a portion of inert ring 700, e.g., a portion of amplifier 100 may be disposed in a portion of connector block 800 wherein a portion of connector block 800 abuts a portion of inert ring 700. Illustratively, a portion of amplifier 100 may be disposed in a portion of connector block 800 wherein connector block distal end 801 is adjacent to inert ring proximal end 702, e.g., a portion of amplifier 100 may be disposed in a portion of connector block 800 wherein connector block distal end 801 abuts inert ring proximal end 702. In one or more embodiments, a portion of amplifier 100 may be disposed in a portion of connector block 800 wherein the portion of amplifier 100 is fixed in the portion of connector block 800, e.g., the portion of amplifier 100 may be fixed in the portion of connector block 800 by a force of friction. Illustratively, a portion of amplifier proximal thread 103 may be disposed in a portion of connector block distal thread 831 wherein the portion of amplifier proximal thread 103 is fixed in the portion of connector block distal thread 831, e.g., the portion of amplifier proximal thread 103 may be fixed in the portion of connector block distal thread 831 by a force of friction. In one or more embodiments, a portion of amplifier 100 may be fixed in a portion of connector block 800 by any suitable fixation means, e.g., a portion of amplifier 100 may be fixed in a portion of connector block 800 by an interference fit, a weld, an adhesive, and epoxy, a crimp, a tie, a pin, etc.

Illustratively, disposing amplifier proximal end 102 beyond a particular distance in connector block 800 may be configured to compress a portion of assembled transducer 1100, e.g., disposing amplifier proximal end 102 beyond a particular distance in connector block 800 may be configured to compress a portion of assembled transducer 1100 dis-posed between connector block distal end 801 and flange interface taper proximal end 112. In one or more embodiments, disposing amplifier proximal end 102 beyond a particular distance in connector block 800 may be configured to apply a force vector to inert ring proximal end 702, e.g., disposing amplifier proximal end 102 beyond a particular distance in connector block 800 may be configured to apply a force vector to inert ring proximal end 702 wherein the force vector is directed towards assembled transducer distal end 1101 and away from assembled transducer proximal end 1102. Illustratively, disposing amplifier proximal end 102 beyond a particular distance in connector block 800 may be configured to apply a force vector to flange distal end 201, e.g., disposing amplifier proximal end 102 beyond a particular distance in connector block 800 may be configured to apply a force vector to flange distal end 201 wherein the force vector is directed towards assembled transducer proximal end 1102 and away from assembled transducer distal end 1101.

In one or more embodiments, disposing amplifier proximal end 102 a first distance beyond a particular distance in connector block 800 may be configured to apply a first force vector to inert ring proximal end 702 wherein the first force vector has a first magnitude. Illustratively, disposing amplifier proximal end 102 a second distance beyond the particular distance in connector block 800 may be configured to apply a second force vector to inert ring proximal end 702 wherein the second force vector has a second magnitude. In one or more embodiments, the second distance beyond the particular distance in connector block 800 may be greater than the first distance beyond the particular distance in connector block 800 and the second magnitude may be greater than the first magnitude.

Illustratively, compressing a portion of assembled transducer 1100 disposed between connector block distal end 801 and flange interface taper proximal end 112 may be configured to increase a contact area between a first surface and a second surface of assembled transducer 1100. In one or more embodiments, compressing a portion of assembled transducer 1100 disposed between connector block distal end 801 and flange inter-face taper proximal end 112 may be configured to increase a contact area between connector block distal end 801 and inert ring proximal end 702. Illustratively, compressing a portion of assembled transducer 1100 disposed between connector block distal end 801 and flange interface taper proximal end 112 may be configured to increase a contact area between inert ring distal end 701 and fifth medial electrical conductor 525. In one or more embodiments, compressing a portion of assembled transducer 1100 disposed between connector block distal end 801 and flange interface taper proximal end 112 may be configured to increase a contact area between fifth medial electrical conductor 525 and fourth piezoelectric ring distal end 401. Illustratively, compressing a portion of assembled transducer 1100 disposed between connector block distal end 801 and flange interface taper proximal end 112 may be configured to increase a contact area between fourth piezoelectric ring proximal end 402 and fourth medial electrical conductor 615. In one or more embodiments, compressing a portion of assembled transducer 1100 disposed between connector block distal end 801 and flange interface taper proximal end 112 may be configured to increase a contact area between fourth medial electrical conductor 615 and third piezoelectric ring proximal end 402. Illustratively, compressing a portion of assembled transducer 1100 disposed between connector block distal end 801 and flange inter-face taper proximal end 112 may be configured to increase a contact area between third piezoelectric ring distal end 401 and third medial electrical conductor 515. In one or more embodiments, compressing a portion of assembled transducer 1100 disposed between connector block distal end 801 and flange interface taper proximal end 112 may be configured to increase a contact area between third medial electrical conductor 515 and second piezoelectric ring distal end 401. Illustratively, compressing a portion of assembled transducer 1100 disposed between connector block distal end 801 and flange interface taper proximal end 112 may be configured to increase a contact area between second piezoelectric ring proximal end 402 and second medial electrical conductor 605. In one or more embodiments, compressing a portion of assembled transducer 1100 disposed between connector block distal end 801 and flange interface taper proximal end 112 may be configured to increase a contact area between second medial electrical conductor 605 and first piezoelectric ring proximal end 402. Illustratively, compressing a portion of assembled transducer 1100 disposed between connector block distal end 801 and flange inter-face taper proximal end 112 may be configured to increase a contact area between first piezoelectric ring distal end 401 and first medial electrical conductor 505. In one or more embodiments, compressing a portion of assembled transducer 1100 disposed between connector block distal end 801 and flange interface taper proximal end 112 may be configured to increase a contact area between first medial electrical conductor 505 and flange proximal end 202. Illustratively, compressing a portion of assembled transducer 1100 disposed between connector block distal end 801 and flange interface taper proximal end 112 may be configured to increase a contact area between flange distal end 201 and flange interface taper proximal end 112.

In one or more embodiments, assembled transducer 1100 may be assembled by disposing amplifier proximal end 102 a first distance in connector block 800, applying a compressive force to a portion of assembled transducer 1100 disposed between connector block distal end 801 and flange interface taper proximal end 112, and disposing amplifier proximal end 102 a second distance in connector block 800 wherein the second distance is greater than the first distance, e.g., a force of friction between amplifier proximal thread 103 and connector block distal thread 831 may be configured to prevent a com-pressed assembled transducer 1100 from decompressing when amplifier proximal end 102 is disposed the second distance in connector block 800. Illustratively, assembled transducer 1100 may be assembled by applying a compressive force in a range of 550 to 2550 pounds to a portion of assembled transducer 1100 disposed between connector block distal end 801 and flange interface taper proximal end 112, e.g., assembled transducer 1100 may be assembled by applying a compressive force of 2000 pounds to a portion of assembled transducer 1100 disposed between connector block distal end 801 and flange inter-face taper proximal end 112. In one or more embodiments, assembled transducer 1100 may be assembled by applying a compressive force of less than 550 pounds or greater than 2550 pounds to a portion of assembled transducer 1100 disposed between connector block distal end 801 and flange interface taper proximal end 112. Illustratively, assembled transducer 1100 may be assembled by applying a compressive force of at least 500 pounds to a portion of assembled transducer 1100 disposed between connector block distal end 801 and flange interface taper proximal end 112. In one or more embodiments, assembled transducer 1100 may be assembled by applying a compressive force of at least 750 pounds to a portion of assembled transducer 1100 disposed between connector block distal end 801 and flange interface taper proximal end 112. Illustratively, assembled transducer 1100 may be assembled by applying a compressive force of at least 1000 pounds to a portion of assembled transducer 1100 disposed between connector block distal end 801 and flange interface taper proximal end 112. In one or more embodiments, assembled transducer 1100 may be assembled by applying a compressive force of at least 1250 pounds to a portion of assembled transducer 1100 disposed between connector block distal end 801 and flange interface taper proximal end 112. Illustratively, assembled transducer 1100 may be assembled by applying a compressive force of at least 1500 pounds to a portion of assembled transducer 1100 disposed between connector block distal end 801 and flange interface taper proximal end 112. In one or more embodiments, assembled transducer 1100 may be assembled by applying a compressive force of at least 1750 pounds to a portion of assembled transducer 1100 disposed between connector block distal end 801 and flange interface taper proximal end 112. Illustratively, assembled transducer 1100 may be assembled by applying a compressive force of at least 2000 pounds to a portion of assembled transducer 1100 disposed between connector block distal end 801 and flange interface taper proximal end 112.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the subject matter set forth herein without departing from its scope. While the dimensions and types of materials described herein are intended to define the parameters of the disclosed subject matter, they are by no means limiting and are exemplary embodiments. Many other embodiments will be apparent to those of skill in the art upon reviewing the above description. The scope of the subject matter described herein should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

As used herein, an element or step recited in the singular and proceeded with the word "a" or "an" should be understood as not excluding plural of said elements or steps, unless such exclusion is explicitly stated. Furthermore, references to "one embodiment" of the presently described subject matter are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

This written description uses examples to disclose several embodiments of the subject matter set forth herein, including the best mode, and also to enable a person of ordinary skill in the art to practice the embodiments of disclosed subject matter, including making and using the devices or systems and performing the methods. The patentable scope of the subject matter described herein is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, communication unit, control system, etc.) may be implemented in a single piece of hardware (for example, a general-purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

Since certain changes may be made in the above-described systems and methods, without departing from the spirit and scope of the inventive subject matter herein involved, it is intended that all of the subject matter of the above description or shown in the accompanying drawings shall be interpreted merely as examples illustrating the inventive concept herein and shall not be construed as limiting the inventive subject matter.

Changes can be made in the above constructions without departing from the scope of the disclosure, it is intended that all matter contained in the above description or shown in the accompanying drawings shall be interpreted as illustrative and not in a limiting sense.

What is claimed is:

1. A control system for an ultrasonic surgical device, comprising:
    a console operatively connected to a power source and configured for detachable connection to the ultrasonic surgical device;
    a control circuit of the console configured to regulate an operating signal to correspond to the operating characteristics of the ultrasonic surgical device in response to a loading signal from the ultrasonic surgical device, wherein the operating signal is configured to be automatically updated based on changes to the loading signal from the ultrasonic surgical device; and
    an operator input of the console operatively connected to the control circuit to provide a control signal based on the operating signal.

2. The control system of claim 1, the control circuit further comprising:
    a drive signal generator configured to produce a generating signal at a drive frequency;
    a drive amplifier operatively connected to the drive signal generator, the drive amplifier configured to provide a drive signal having a drive voltage and a drive current in response to the operating signal;
    a first phase comparator operatively connected to the drive signal generator and operatively connected to the drive amplifier, the first phase comparator configured to provide a phase adjustment signal based on a comparison of the drive voltage and the drive current;
    a drive tuning circuit operatively connected to the drive amplifier and configured to provide a tuned drive signal in response to the phase adjustment signal;
    a device loading circuit operatively connected to the drive tuning circuit and operatively connected to the ultrasonic surgical device, the device loading circuit being configured to provide an operating signal to the ultrasonic surgical device, and provide a loading signal in response to the operating characteristics of the ultrasonic surgical device; and
    a second phase comparator operatively connected to the drive amplifier and operatively connected to the device loading circuit, the second phase comparator being configured provide a frequency adjustment signal to the drive signal generator based on a comparison of the drive current to the loading signal.

3. The control system of claim 1, wherein the operating signal is automatically adjusted during operation based on the operating characteristics of the ultrasonic surgical device.

4. The control system of claim 1, wherein the control system includes a feedback loop to monitor the loading signal and update the operating signal in real time during operation of the ultrasonic surgical device.

5. The control system of claim 1, wherein the control circuit includes a phase comparator configured to provide a frequency adjustment signal based on a comparison of a drive current and the loading signal, wherein the operating signal is updated based on the frequency adjustment signal.

6. The control system of claim 1, wherein the control circuit generates a calibration signal to calibrate the control circuit based on the operating characteristics of the ultrasonic surgical device.

7. The control system of claim 1, wherein the control circuit includes an analog circuit configured to control power in response to a load of the ultrasonic surgical device, the control circuit comprising a digital circuit configured to automatically adjust a frequency of the analog circuit calibrated to a resonance frequency of the ultrasonic surgical device.

8. The control system of claim 1, wherein the operating signal is updated during operation of the ultrasonic surgical device corresponding to operating characteristics of the ultrasonic surgical device based on thermal expansion of the ultrasonic surgical device.

9. The control system of claim 1, wherein the operating signal is updated during operation of the ultrasonic surgical device corresponding to operating characteristics of the ultrasonic surgical device based on signal fluctuations of the operating signal.

10. The control system of claim 1, wherein the operating signal is updated during operation of the ultrasonic surgical device corresponding to operating characteristics of the ultrasonic surgical device based on environmental factors surrounding the ultrasonic surgical device.

11. The control system of claim 1, further comprising an ultrasonic surgical device connected to the console by a connection assembly, the ultrasonic surgical device comprising an ultrasonic tip at a working plane at an end of the ultrasonic surgical device.

12. The control system of claim 11, wherein the ultrasonic surgical device includes a motor having a torsional transducer assembly along a central axis of the surgical device, the motor being operatively connected to the console and being operated based on the operating signal, wherein the motor is configured to create a standing wave along a central axis of the ultrasonic surgical device in response to an application of an electrical current and voltage from the power source, the standing wave creates motion of the ultrasonic tip about the central axis at the working plane, the standing wave defining an alternating pattern of nodes and anti-nodes along the central axis, wherein a position of one of the anti-nodes along a center axis corresponds with the position of the working plane.

13. The control system of claim 12, wherein the standing wave creates torsional motion of the ultrasonic tip.

14. The control system of claim 12, wherein the ultrasonic surgical device includes a surgical attachment having an angled adaptor having a junction positioned to correspond with one of the nodes of the standing wave.

15. The control system of claim 2, wherein the control system includes a feedback loop to monitor the loading signal and update the operating signal in real time during operation of the ultrasonic surgical device.

16. The control system of claim 2, wherein the control circuit includes an analog circuit configured to control power in response to a load of the ultrasonic surgical device, the control circuit comprising a digital circuit configured to automatically adjust a frequency of the analog circuit calibrated to a resonance frequency of the ultrasonic surgical device.

17. The control system of claim 2, further comprising an ultrasonic surgical device connected to the console by a connection assembly, the ultrasonic surgical device comprising an ultrasonic tip at a working plane at an end of the ultrasonic surgical device.

18. The control system of claim 17, wherein the ultrasonic surgical device includes a motor having a torsional transducer assembly along a central axis of the surgical device, the motor being operatively connected to the console and being operated based on the operating signal, wherein the motor is configured to create a standing wave along a central axis of the ultrasonic surgical device in response to an application of an electrical current and voltage from the power source, the standing wave creates motion of the ultrasonic tip about the central axis at the working plane, the standing wave defining an alternating pattern of nodes and anti-nodes along the central axis, wherein a position of one of the anti-nodes along the center axis corresponds with the position of the working plane.

19. The control system of claim 18, wherein the ultrasonic surgical device includes a surgical attachment having an angled adaptor having a junction positioned to correspond with one of the nodes of the standing wave.

20. A control system for an ultrasonic surgical device comprising:
　a console operatively connected to a power source and configured for detachable connection to the ultrasonic surgical device;
　a control circuit of the console configured to regulate an operating signal to correspond to operating characteristics of the ultrasonic surgical device in response to a loading signal from the ultrasonic surgical device, wherein the operating signal is configured to be automatically updated based on changes to the loading signal from the ultrasonic surgical device; and
　a phase comparator operatively connected to a drive amplifier and operatively connected to a device loading circuit, wherein the drive amplifier is configured to provide a drive signal having a drive voltage and a drive current in response to the operating signal, and wherein the phase comparator is configured provide a frequency adjustment signal to a drive signal generator based on a comparison of the drive current to the loading signal.

21. A control system comprising:
an ultrasonic surgical device having a connection assembly, wherein the ultrasonic surgical device comprises an ultrasonic tip at a working plane at an end of the ultrasonic surgical device, the ultrasonic surgical device having an ultrasonic transducer assembly causing ultrasonic motion of the ultrasonic tip;
a console operatively connected to a power source, wherein the connection assembly of the ultrasonic surgical device is detachably coupled to the console;
a control circuit configured to regulate an operating signal to correspond to operating characteristics of the ultrasonic surgical device in response to a loading signal from the ultrasonic surgical device; and
an operator input of the console operatively connected to the control circuit to provide a control signal for controlling the ultrasonic surgical device.

* * * * *